(12) United States Patent
de Juan et al.

(10) Patent No.: US 11,906,719 B2
(45) Date of Patent: Feb. 20, 2024

(54) DEVICES, SYSTEMS, AND METHODS FOR TREATING EAR DISORDERS

(71) Applicant: Spiral Therapeutics Inc., Brisbane, CA (US)

(72) Inventors: Eugene de Juan, Brisbane, CA (US); Hugo Peris, Brisbane, CA (US); Signe Erickson, Brisbane, CA (US); Vrad Levering, Brisbane, CA (US)

(73) Assignee: Spiral Therapeutics Inc., South San Francisco, CA (US)

( * ) Notice: Subject to any disclaimer, the term of this patent is extended or adjusted under 35 U.S.C. 154(b) by 395 days.

(21) Appl. No.: 17/155,589

(22) Filed: Jan. 22, 2021

(65) Prior Publication Data

US 2021/0228235 A1    Jul. 29, 2021

Related U.S. Application Data

(60) Provisional application No. 63/082,996, filed on Sep. 24, 2020, provisional application No. 63/081,015, (Continued)

(51) Int. Cl.
*A61B 1/227* (2006.01)
*A61B 1/018* (2006.01)
(Continued)

(52) U.S. Cl.
CPC .......... *G02B 21/0012* (2013.01); *A61B 1/018* (2013.01); *A61B 1/227* (2013.01);
(Continued)

(58) Field of Classification Search
CPC  G02B 21/0012; G02B 21/0032; G02B 21/22; G02B 23/2476; A61B 1/018;
(Continued)

(56) References Cited

U.S. PATENT DOCUMENTS 5,421,818 A    6/1995  Arenberg
6,024,726 A    2/2000  Hill
(Continued)

FOREIGN PATENT DOCUMENTS

WO    WO 2008097317    8/2008
WO    WO 2019086608    5/2019
(Continued)

OTHER PUBLICATIONS

International Search Report and Written Opinion in International Appln. No. PCT/US2021/14612, dated Jul. 8, 2021, 11 pages.
(Continued)

*Primary Examiner* — Amber R Stiles
(74) *Attorney, Agent, or Firm* — Fish & Richardson P.C.

(57) ABSTRACT

Systems and methods can be employed for trans-tympanic membrane access to the middle ear for delivery of a formulation or implant device to a target location under direct visualization. The systems and methods can also be used to improve accessibility and visualization for various otological surgical procedures, such as, but not limited to, cholesteatoma removal, tympanic membrane repair and ossicular chain repair.

17 Claims, 15 Drawing Sheets

Related U.S. Application Data filed on Sep. 21, 2020, provisional application No. 63/080,510, filed on Sep. 18, 2020, provisional application No. 63/078,141, filed on Sep. 14, 2020, provisional application No. 63/077,448, filed on Sep. 11, 2020, provisional application No. 63/051,568, filed on Jul. 14, 2020, provisional application No. 63/040,495, filed on Jun. 17, 2020, provisional application No. 63/024,183, filed on May 13, 2020, provisional application No. 62/965,481, filed on Jan. 24, 2020.

(51) Int. Cl.
| | | |
|---|---|---|
| *G02B 21/00* | (2006.01) | |
| *G02B 21/22* | (2006.01) | |
| *A61B 17/29* | (2006.01) | |
| *A61M 31/00* | (2006.01) | |
| *A61B 17/34* | (2006.01) | |
| *A61M 37/00* | (2006.01) | |
| *A61B 17/32* | (2006.01) | |
| *A61B 18/04* | (2006.01) | |
| *A61B 18/20* | (2006.01) | |
| *A61F 2/958* | (2013.01) | |
| *A61B 17/3205* | (2006.01) | |
| *A61B 18/14* | (2006.01) | |
| *A61F 11/20* | (2022.01) | |
| *A61B 17/00* | (2006.01) | |
| *A61B 18/00* | (2006.01) | |
| *A61F 2/18* | (2006.01) | |

(52) U.S. Cl.
CPC .......... *A61B 17/29* (2013.01); *A61B 17/3205* (2013.01); *A61B 17/320068* (2013.01); *A61B 17/3423* (2013.01); *A61B 17/3468* (2013.01); *A61B 17/3478* (2013.01); *A61B 18/04* (2013.01); *A61B 18/1485* (2013.01); *A61B 18/20* (2013.01); *A61F 2/958* (2013.01); *A61F 11/20* (2022.01); *A61F 11/202* (2022.01); *A61M 31/00* (2013.01); *A61M 31/002* (2013.01); *A61M 37/0015* (2013.01); *G02B 21/0032* (2013.01); *G02B 21/22* (2013.01); *A61B 2017/00115* (2013.01); *A61B 2017/00787* (2013.01); *A61B 2017/00867* (2013.01); *A61B 2017/32007* (2017.08); *A61B 2018/00327* (2013.01); *A61B 2217/005* (2013.01); *A61F 2002/183* (2013.01); *A61F 2250/0067* (2013.01); *A61M 2037/0023* (2013.01); *A61M 2037/0046* (2013.01); *A61M 2205/04* (2013.01); *A61M 2210/0662* (2013.01); *A61M 2210/0668* (2013.01)

(58) Field of Classification Search
CPC . A61B 1/227; A61B 17/29; A61B 17/320068; A61B 17/3205; A61B 17/3423; A61B 17/3468; A61B 17/3478; A61B 18/04; A61B 18/1485; A61B 18/20; A61B 2017/00115; A61B 2017/00787; A61B 2017/00867; A61B 2017/32007; A61B 2018/00327; A61B 2217/005; A61B 2017/00323; A61B 2017/00331; A61B 2017/345; A61F 2/958; A61F 11/20; A61F 11/202; A61F 2002/183; A61F 2250/0067; A61F 11/00; A61M 31/00; A61M 31/002; A61M 37/0015; A61M 2037/0023; A61M 2037/0046; A61M 2205/04; A61M 2210/0662; A61M 2210/0668

See application file for complete search history.

(56) References Cited

U.S. PATENT DOCUMENTS

| | | | |
|---|---|---|---|
| 6,045,528 A | 4/2000 | Arenberg et al. | |
| 6,120,484 A | 9/2000 | Silverstein | |
| 6,440,102 B1 | 8/2002 | Arenberg et al. | |
| 6,648,873 B2 | 11/2003 | Arenberg et al. | |
| 7,351,246 B2 | 4/2008 | Epley | |
| 7,704,259 B2 | 4/2010 | Kaplan et al. | |
| 8,197,461 B1 | 6/2012 | Arenberg et al. | |
| 9,352,084 B2 | 5/2016 | Decker et al. | |
| 9,616,207 B2 | 4/2017 | Verhoeven et al. | |
| 10,130,514 B2 | 11/2018 | Imran et al. | |
| 10,492,670 B1 | 12/2019 | Bendory et al. | |
| 2003/0220536 A1 | 11/2003 | Hissong | |
| 2004/0172005 A1 | 9/2004 | Arenberg et al. | |
| 2008/0262510 A1* | 10/2008 | Clifford | A61N 1/306 604/501 |
| 2011/0224629 A1 | 9/2011 | Jolly et al. | |
| 2012/0203200 A1 | 8/2012 | Kenney et al. | |
| 2013/0060131 A1 | 3/2013 | Oghalai et al. | |
| 2013/0245569 A1 | 9/2013 | Jolly et al. | |
| 2016/0346511 A1 | 12/2016 | Cohen et al. | |
| 2017/0172804 A1 | 6/2017 | Watanabe et al. | |
| 2019/0015254 A1 | 1/2019 | Bendory et al. | |
| 2019/0321610 A1 | 10/2019 | Goldfarb et al. | |
| 2020/0094030 A1 | 3/2020 | Kim et al. | |

FOREIGN PATENT DOCUMENTS

| | | |
|---|---|---|
| WO | WO 2019152866 | 8/2019 |
| WO | WO 2019200259 | 10/2019 |
| WO | WO 2020115674 | 6/2020 |

OTHER PUBLICATIONS

PCT Invitation to Pay Fees in International Appln. No. PCT/US2021/014618, dated Apr. 1, 2021, 3 pages.

* cited by examiner

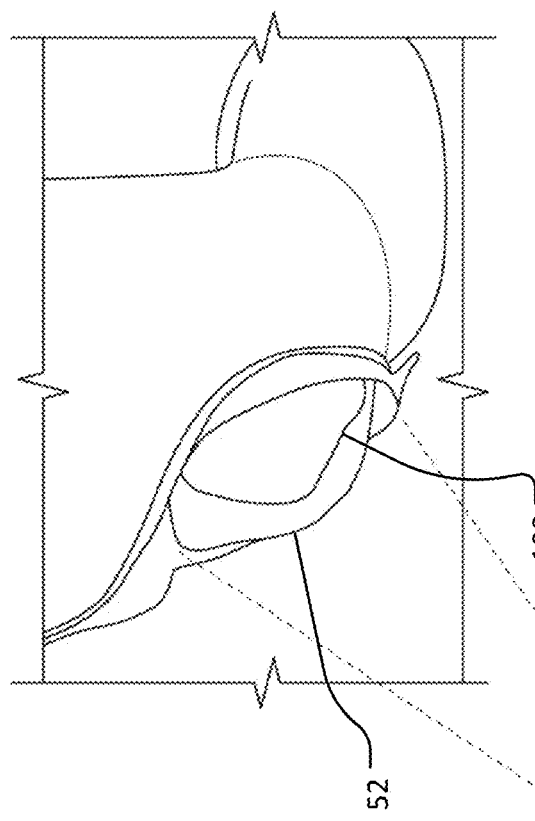
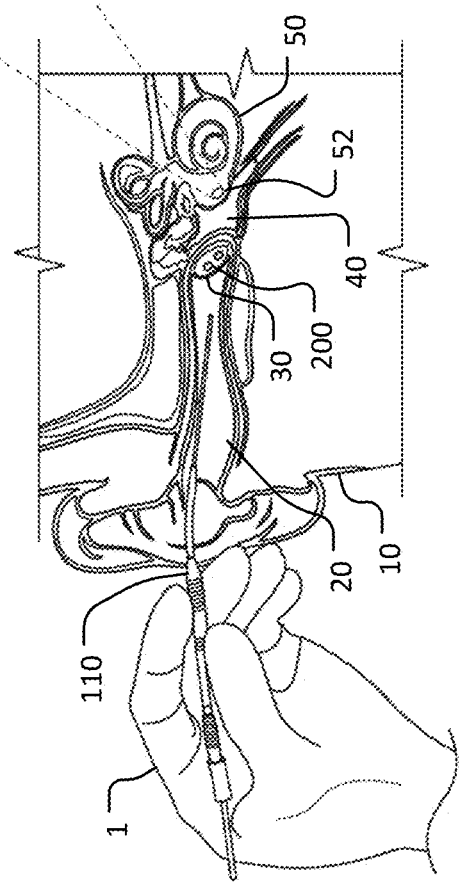
FIG. 1
FIG. 2

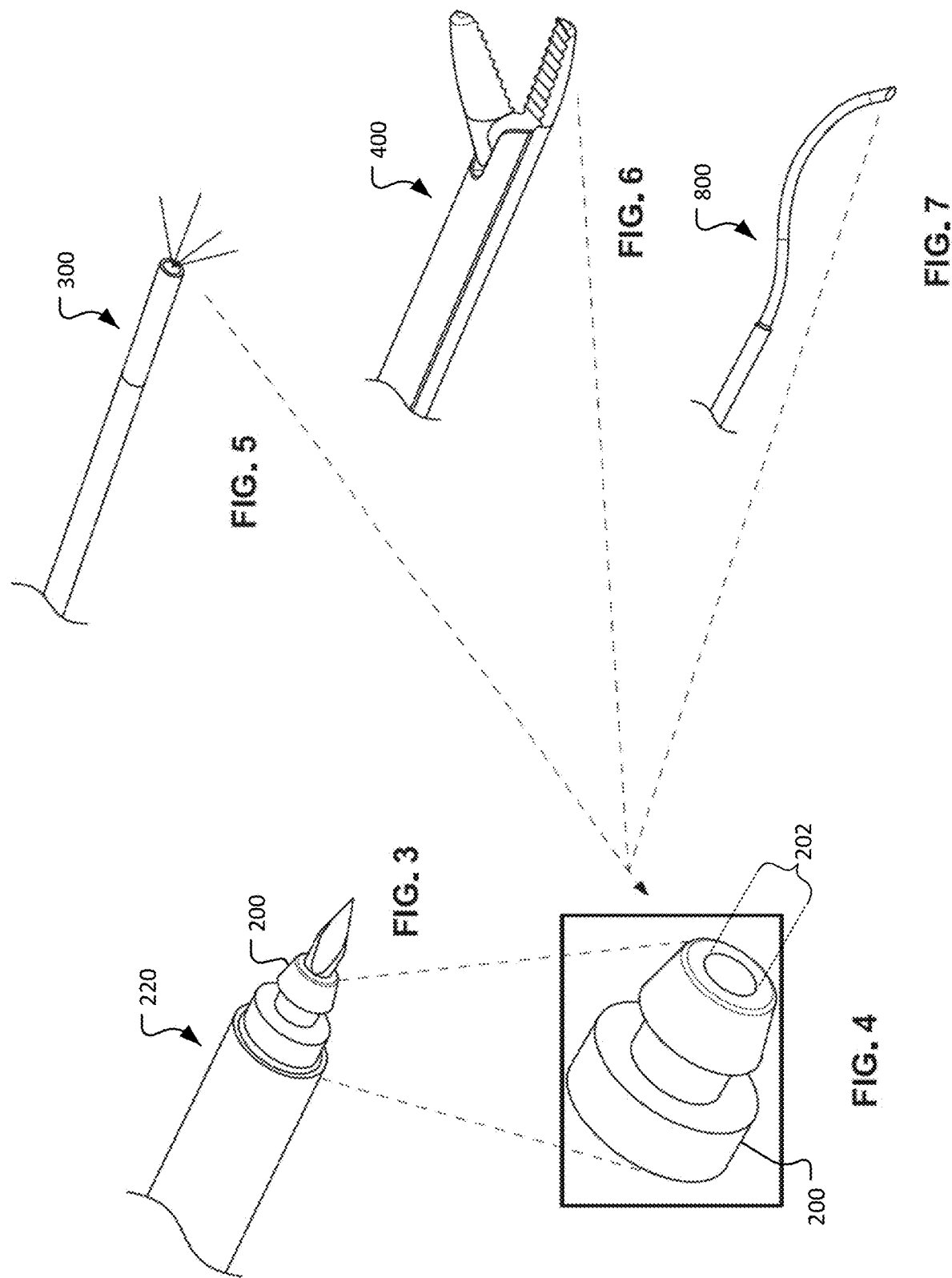

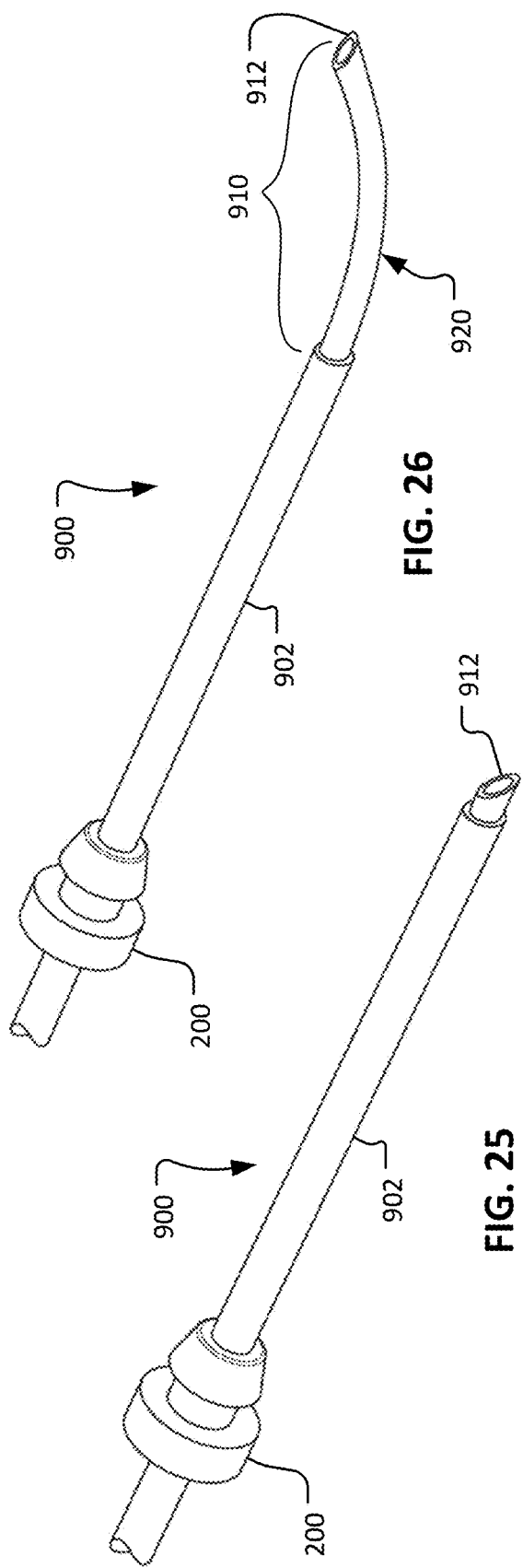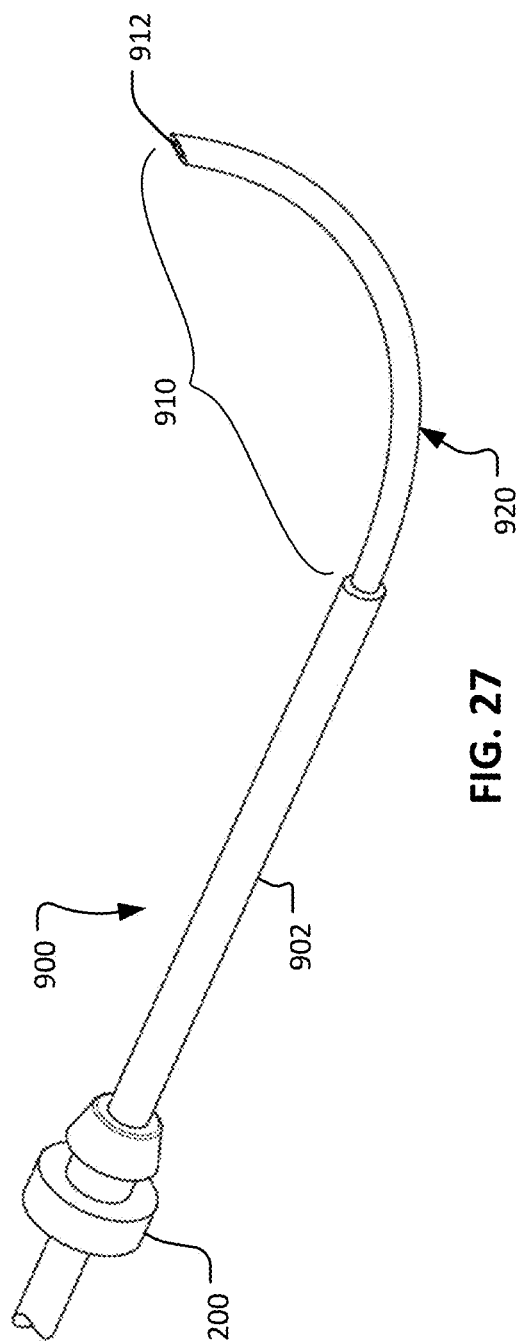

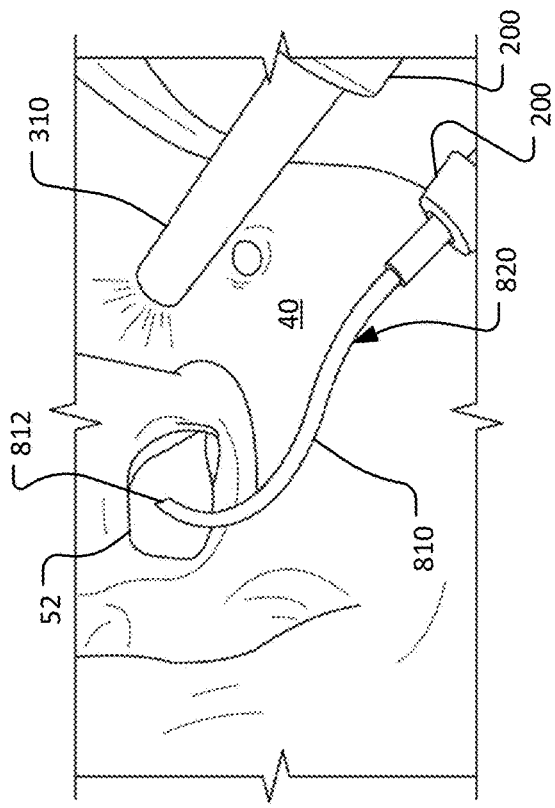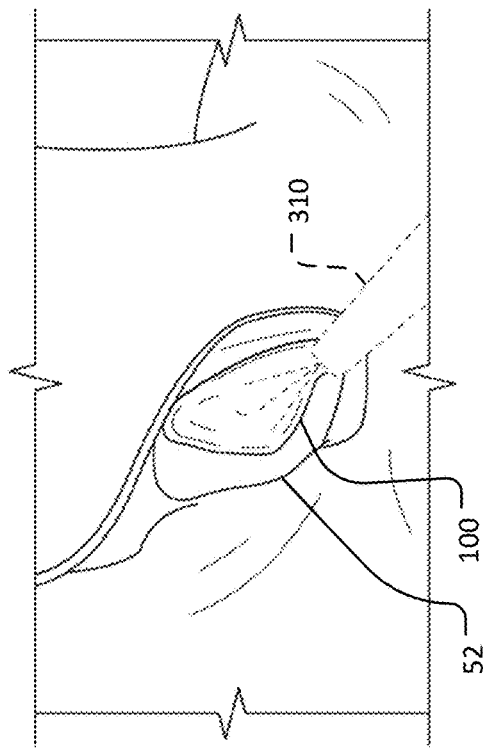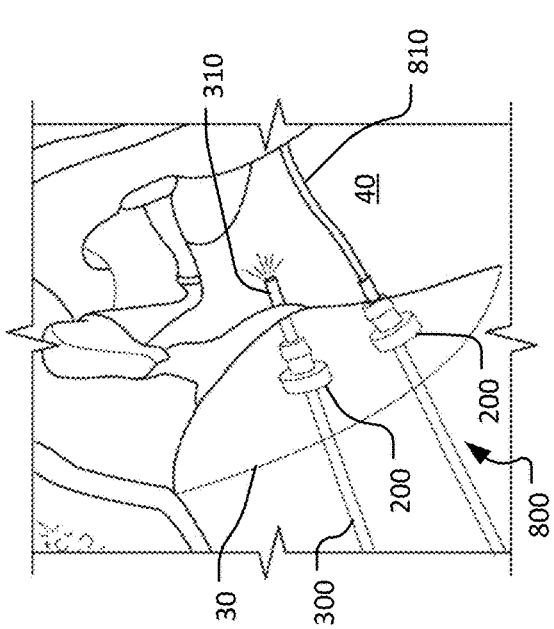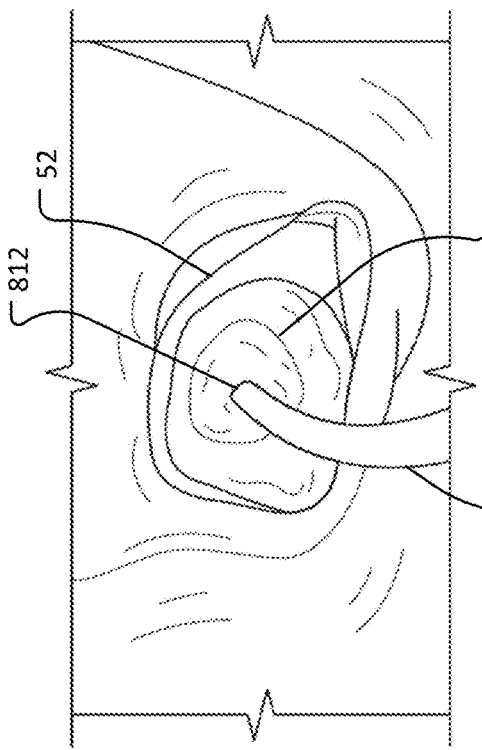

DEVICES, SYSTEMS, AND METHODS FOR TREATING EAR DISORDERS

CROSS-REFERENCE TO RELATED APPLICATIONS

This application claims the benefit of priority to U.S. Provisional Application No. 62/965,481 filed on Jan. 24, 2020, U.S. Provisional Application No. 63/024,183 filed on May 13, 2020 (which is fully incorporated herein by reference), U.S. Provisional Application No. 63/040,495 filed on Jun. 17, 2020 (which is fully incorporated herein by reference), U.S. Provisional Application No. 63/051,568 filed on Jul. 14, 2020 (which is fully incorporated herein by reference), U.S. Provisional Application No. 63/077,448 filed on Sep. 11, 2020 (which is fully incorporated herein by reference), U.S. Provisional Application No. 63/078,141 filed on Sep. 14, 2020 (which is fully incorporated herein by reference), U.S. Provisional Application No. 63/080,510 filed on Sep. 18, 2020 (which is fully incorporated herein by reference), U.S. Provisional Application No. 63/081,015 filed on Sep. 21, 2020 (which is fully incorporated herein by reference), and U.S. Provisional Application No. 63/082,996 filed on Sep. 24, 2020 (which is fully incorporated herein by reference).

TECHNICAL FIELD

This document relates to devices, systems, methods, and materials for treating ear disorders including, but not limited to hearing loss. In some examples, the systems and methods include trans-tympanic membrane access to the middle ear and/or inner ear for targeted delivery of an implant device or a formulation under direct visualization.

BACKGROUND

The human ear is subject to a variety of disorders including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, outer ear infections, middle ear infections, schwannoma, and tympanic membrane perforations, to provide a few examples.

In one example, Conductive Hearing Loss (CHL) involves the loss of normal mechanical pathways for sound to reach the hair cells in the cochlea, for example due to malformation, accumulation of fluid in the middle ear, disruption of the tympanic membrane, presence of tumors, and/or damage to ossicles. SensoriNeural Hearing Loss (SNHL) is due to the absence of, or damage to, hair cells in the cochlea, or to the acoustic nerve. SNHL is typically associated with exposure to loud noise, head trauma, aging, infection, Meniere's Disease, tumors, ototoxicity, genetic diseases like Usher's disease, and the like.

SUMMARY

This document describes devices, systems, and methods for minimally invasive access to the middle ear for purposes of delivering treatment for inner and/or middle ear disorders. For example, this document describes devices, systems, and methods for trans-tympanic membrane access to achieve minimally invasive delivery of formulations or implant devices (which can deliver formulations). In some implementations, the formulations or implant devices are delivered into the round window niche and adjacent to the round window membrane of the cochlea under direct visualization. In particular implementations, the active agent of the formulation and/or implant device may then transfer passively by diffusion across the round window membrane(s), according to a concentration gradient, into the perilymph (within the cochlea).

In some embodiments, the formulations or implant devices are delivered into other targeted areas of the middle and/or inner ear such as, but not limited to, the oval window. In particular embodiments, the formulations or implant devices can be placed directly into the inner ear (perilymph) by injecting across the oval window, the round window, or to other parts of the cochlea through or a cochleostomy, with or without the use of microneedles.

The devices, systems, materials, compounds, compositions, articles, and methods described herein may be used to treat a variety of disorders of the middle ear and/or inner ear including, but not limited to, hearing loss, tinnitus, balance disorders including vertigo, Meniere's Disease, vestibular neuronitis, vestibular schwannoma, labyrinthitis, otosclerosis, ossicular chain dislocation, cholesteatoma, middle ear infections, perilymph fistula, and tympanic membrane perforations, to provide a few examples.

In one aspect, this disclosure is directed to a system for delivering a formulation or an implant adjacent to a cochlea of a patient. The system can include: (i) first and second tympanic membrane port devices configured to be removably implanted in spaced apart positions in a tympanic membrane of the patient, the first tympanic membrane port device defining a first lumen and the second tympanic membrane port device defining a second lumen; (ii) an endoscope slidable through the first lumen of the first tympanic membrane port device while the first tympanic membrane port is implanted in the tympanic membrane such that a distal end portion of the endoscope is positionable in a middle ear to visualize a target region of the middle ear or an inner ear; and (iii) an instrument slidable through the second lumen of the second tympanic membrane port device while the second tympanic membrane port device is implanted in the tympanic membrane such that a distal tip portion of the instrument is advanceable to the target region, the instrument configured to deliver the formulation or implant to the target region while the distal end portion of the endoscope in the middle ear is spaced apart from the instrument to provide visualization of the instrument.

Such a system for delivering a formulation or an implant adjacent to a cochlea of a patient may optionally include one or more of the following features. The system may also include a tympanic membrane port insertor configured to removably implant the first and second tympanic membrane port devices in the tympanic membrane. The tympanic membrane port insertor may include an elongate delivery sheath, a pusher catheter, and a trocar needle. In some embodiments, the pusher catheter is slidably disposed within a lumen defined by the delivery sheath. The trocar needle may be slidably disposed within a lumen defined by the pusher catheter. An outer diameter of the trocar needle may be less than an inner diameter of the first and second lumens of the first and second tympanic membrane port devices. An outer diameter of the pusher catheter may be greater than the inner diameter of the first and second lumens of the first and second tympanic membrane port devices. In some embodiments, the distal tip portion of the injector instrument includes a single curve. In some embodiments, the distal tip portion of the injector instrument includes a first curved portion and a second curved portion. The first and second curved portions may be in a same plane and curve in opposing directions. The system may also include a membrane modification instrument slidable through the second lumen of the second tympanic membrane port device while the second tympanic membrane port device is implanted in the tympanic membrane such that a distal tip portion of the membrane modification instrument is advanceable to the round window niche. The membrane modification instrument may be configured for tearing a pseudomembrane at a round window niche while the distal end portion of the endoscope in the middle ear is spaced apart from the membrane modification instrument and provides visualization of the membrane modification instrument.

In another aspect, this disclosure is directed to a system for delivering formulation at a target location in a middle or inner ear of a patient. The system can include: (a) an endoscope including an endoscope shaft with a distal tip portion sized to be positioned within a middle ear; (b) a sleeve device defining: (i) a first lumen configured to slidably receive the endoscope shaft and (ii) a second lumen; (c) an injection device including a proximal actuator and an injection shaft with a distal tip portion defining a distal delivery port, the injection shaft sized to be slidably received in the second lumen of the sleeve device, the distal tip portion of the injection shaft being adjustable from a longitudinally straight shape to a curved shape to orient the distal delivery port at the target location in the middle or inner ear; and (d) a formulation source in fluid communication with the injection device so that the distal delivery port is configured to deliver the formulation at the target location while the distal tip portion of the injection device is arranged in the curved shape.

Such a system for delivering formulation at a target location in a middle or inner ear of a patient may optionally include one or more of the following features. The distal tip portion of the injection device may have shape memory to seek the curved shape. The distal tip portion of the injection device may be selectively adjustable to the curved shape by manipulating one or more control members slidably coupled within lumens defined by the distal tip portion. The system may also include a first tympanic membrane port device configured to be removably implanted in the tympanic membrane of the patient. The first membrane port device may define a first lumen, and the sleeve device may be configured to pass through the first lumen. In some embodiments, the sleeve device is configured to pass through the first lumen while the endoscope is within the first lumen and the injection device is within the second lumen.

In another aspect, this disclosure is directed to a system for delivering an implant device to a target location in a middle or inner ear of a patient. The system can include: an endoscope including an endoscope shaft with a distal tip portion sized to be positioned within a middle ear; a sleeve device defining: (i) a first lumen configured to slidably receive the endoscope shaft and (ii) a second lumen; and an implant delivery device including a proximal actuator and a shaft with a distal tip portion configured to releasably couple with an implant device. The shaft can be sized to be slidably received in the second lumen of the sleeve device. The distal tip portion of the implant delivery device can be adjustable from a longitudinally straight shape to a curved shape to orient the distal tip portion at the target location in the middle or inner ear.

Such a system for delivering an implant device to a target location in a middle or inner ear of a patient may optionally include one or more of the following features. The system may also include the implant device. The implant device maybe solid or semisolid with one or more therapeutic agents dispersed within. The implant device may be comprised of a solid drug matrix surrounded by drug permeable materials and drug impermeable materials. The implant device may be comprised of a metal or polymer core with a drug eluting coating applied. The implant device may include an array of microneedles that act as a permeation enhancer.

In another aspect, this disclosure is directed to a method of treating an ear disorder of a patient. The method can include: advancing a trocar needle carrying a first tympanic membrane port device into an outer ear of the patient; creating a first puncture opening in a tympanic membrane of the patient using a distal tip portion of the trocar needle while the trocar needle is carrying the first tympanic membrane port device; advancing the distal tip portion of the trocar needle through the puncture opening to implant the first tympanic membrane port device in the tympanic membrane, the first tympanic membrane port device defining a first lumen therethrough; advancing an injector instrument into the outer ear of the patient and the first lumen until a distal tip of the injector instrument is adjacent to a target location in a middle ear or inner ear of the patient; and delivering, via the injector instrument, a formulation or an implant device at the target location.

Such a method of treating an ear disorder of a patient may optionally include one or more of the following features. In some embodiments, the advancing an injector instrument and the delivering the formulation or the implant device are each performed while an endoscope provides directed visualization of the target location and of the injector instrument proximate to the target location.

In another aspect, this disclosure is directed to an otic implant device sized and shaped to anchor to a portion of a cochlea and having a refillable reservoir containing a formulation for sustained released to a round window niche of the cochlea.

Such an otic implant device may optionally include one or more of the following features. The implant device may be solid. The implant device may be semisolid. The implant device may be comprised of a solid drug matrix surrounded by drug permeable materials and drug impermeable materials. The implant device may be comprised of a metal or polymer core with a drug eluting coating applied. The implant device may include an array of microneedles that act as a permeation enhancer.

In another aspect, this disclosure is directed to a system for delivering an implant device to a round window niche of a patient. The system can include: an endoscope including an endoscope shaft with a distal tip portion sized to be positioned within a middle ear of the patient; an implant device having a reservoir containing a formulation for sustained released to the round window niche; and an implant delivery device including a proximal actuator and a shaft with a distal tip portion configured to releasably couple with the implant device. The distal tip portion of the implant delivery device can be adjustable from a longitudinally straight shape to a curved shape to orient the distal tip portion at the round window niche.

Some or all of the embodiments described herein may provide one or more of the following advantages. First, the systems and methods for treating hearing loss, and all other ear disorders as described herein, can include specialized techniques and instruments that can be used to access the middle and/or inner ear and to precisely deliver a formulation to a target location. The systems and methods for treating hearing loss, and all other ear disorders as described herein, can also include specialized techniques and instruments that can be used to access the middle and/or inner ear and to precisely place a solid implant or sustained delivery system across on or across the round window membrane, oval window, or to other parts of the cochlea through a cochleostomy. The systems and methods for treating hearing loss, and all other ear disorders as described herein, can also include specialized techniques and instruments that can be used to precisely deliver formulations and/or implant devices to other parts of the middle ear cavity.

Second, the systems and methods for treating hearing loss described herein deliver formulations and/or implant devices to the middle and/or inner ear under direct visualization. The use of such direct visualization advantageously allows visual confirmation of the proper placement of the formulations and/or implant devices with a high level of accuracy. The direct visualization also provides additional benefits such as the ability to ascertain visually whether there are any obstructions that could inhibit the proper delivery of the formulations and/or implant devices. For example, in some cases the round window is covered by a pseudomembrane that can be altered or moved to allow improved access to the round window niche. By using the improved instrumentation described herein, the presence of the pseudomembrane can be visually verified, and thereafter physically altered or moved, so that improved and direct access to the round window niche can be visually verified. In addition, after the formulation and/or implant device has been administered, direct visualization can be used to verify that the formulation and/or implant device is/are retained in the desired position and manner.

Third, the systems and methods for treating hearing loss and other ear disorders as described herein allow direct access to the middle ear cavity through the tympanic membrane in a suture-less, low impact manner. In some implementations, such direct access through the tympanic membrane using tympanic membrane port devices can be safer, less invasive, and achieved with no sealing or patching of the tympanic membrane after removal of the tympanic membrane port devices. For example, due to the small size of the tympanic membrane port devices, the tympanic membrane can heal naturally after removal of the tympanic membrane port devices.

Fourth, the systems and methods for treating hearing loss and other ear disorders as described herein facilitate treatments in a minimally invasive fashion. Such minimally invasive techniques can tend to reduce recovery times, patient discomfort, and treatment costs. Moreover, the methods described herein can be performed using a local anesthetic rather than requiring general anesthesia. Accordingly, the treatment cost, patient risks, and recovery times are further advantageously reduced.

Fifth, the systems described herein can also be used for diagnostic purposes. Such uses can help in procedure planning, change site of care, and potentially improve patient outcomes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic illustration of a medical procedure for treating hearing loss, in accordance with some embodiments.

FIG. 2 shows a perspective view of a therapeutic gel substance residing within a cochlea and that was delivered via a round window of the cochlea in accordance with the procedure of FIG. 1.

FIG. 3 shows a perspective view of an example tympanic membrane port device mounted on a delivery trocar in accordance with some embodiments.

FIG. 4 shows a perspective view of the tympanic membrane port device of FIG. 3.

FIG. 5 shows a perspective view of an example endoscope instrument with a distal viewing tip that is configured to be advanced into the middle ear via the tympanic membrane port device of FIG. 3.

FIG. 6 shows a perspective view of an example membrane modification instrument that is configured to be advanced into the middle ear via the tympanic membrane port device of FIG. 3.

FIG. 7 shows a perspective view of an example therapeutic agent injector instrument that is configured to be advanced into the middle ear via the tympanic membrane port device of FIG. 3.

FIG. 25 shows an example injection device extending through an example tympanic membrane port device and in a first configuration.

FIG. 26 shows the example injection device of FIG. 25 extending through an example tympanic membrane port device and in a second configuration.

FIG. 27 shows the example injection device of FIG. 25 extending through an example tympanic membrane port device and in a third configuration.

FIG. 28 shows the two tympanic membrane port devices in the patient's tympanic membrane (in accordance with FIG. 11), an example endoscope device extending through a first one of the tympanic membrane port devices, and an example injection device extending through a second one of the tympanic membrane port devices.

FIG. 29 shows the injection device of FIG. 28 extended and oriented in preparation for injecting a therapeutic agent into the round window of the patient's cochlea.

FIG. 30 shows the injection device of FIG. 28 delivering a dose of the therapeutic agent into the round window of the patient's cochlea.

FIG. 31 shows an example light energy delivery device that is projecting light energy onto the therapeutic agent to photo-cure the therapeutic agent as a gel.

Like reference symbols in the various drawings indicate like elements.

DETAILED DESCRIPTION OF ILLUSTRATIVE EMBODIMENTS

Figure 8:
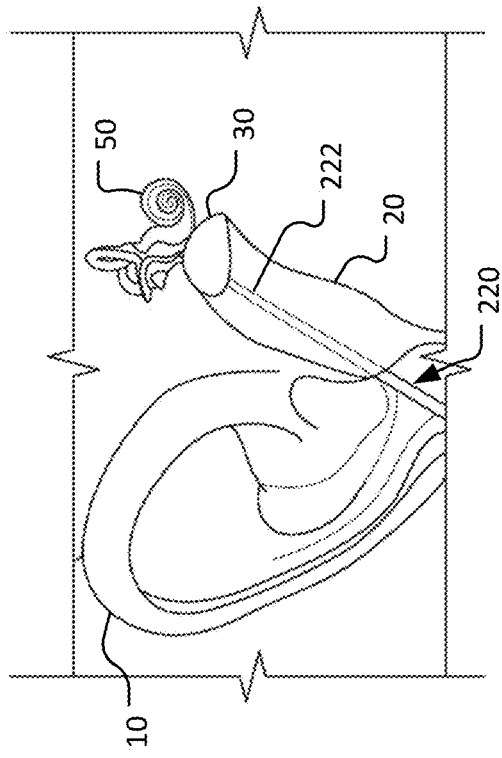
FIG. 8 shows a patient in position for the medical procedure for treating hearing loss and other ear disorders as described herein.

Referring now to FIGS. 1-2, particular embodiments of systems and methods for treating a patient 10 can include an improved set of medical instruments and techniques for delivering a formulation 100 containing a therapeutic agent or active ingredient (or an implantable device that releases such a formulation) to a targeted site of the patient 10, for example, under direct endoscopic visualization. As described herein, in some cases the formulation 100 is a liquid or gel, and the targeted site is a round window niche of a cochlea 50. However, the inventive concepts disclosed herein are not so limited. That is, while the inventive concepts are primarily described in the example context of the delivery of a liquid or gel formulation to the round window niche of the cochlea 50, it should be understood that the inventive aspects disclosed herein are broader than those particular examples. For instance, in some cases the targeted site is elsewhere in the middle and/or inner ear regions such as, but not limited to, the oval window, other parts of the cochlea through a cochleostomy, or to other regions of the middle and/or inner ear. Moreover, in some cases an implantable device (also referred to herein as an "implant device," a "solid implant," or an "implant") is delivered using the devices, systems, and methods described herein. Such an implant may release a therapeutic agent over a period of time. Accordingly, it should be understood that the devices, systems, materials, compounds, compositions, articles, and methods described herein are applicable to the delivery of formulations and/or implants to any/all regions of the middle and/or inner ear.

The devices, systems, and methods described herein can be used to treat and/or prevent a variety of conditions, including but not limited to hearing loss, including hidden hearing loss, noise-induced hearing loss, age-related hearing loss, drug-induced hearing loss (e.g., chemotherapy-induced hearing loss or aminoglycoside-induced hearing loss), sudden sensorineural hearing loss (SNHL), autoimmune inner ear disease, cholesteatoma, and the like.

While the devices, systems, materials, compounds, compositions, articles, and methods are described herein primarily in the context of treating and/or preventing hearing loss, it should be understood that devices, systems, materials, compounds, compositions, articles, and methods can also be used to treat and/or prevent any other disorder of the middle ear and/or inner ear including, but not limited to, tinnitus, balance disorders including vertigo, Meniere's Disease, vestibular neuronitis, vestibular schwannoma, labyrinthitis, otosclerosis, ossicular chain dislocation, cholesteatoma, middle ear infections, and tympanic membrane perforations, to provide a few examples.

This disclosure describes treatment methods and devices for treating the patient 10 using a minimally invasive approach. As depicted in FIG. 1, a clinician 1 approaches the cochlea 50 via the patient's 10 outer ear canal 20 using various instruments as described further below (collectively represented here by a generic instrument 110). The instruments 110 are advanced through the tympanic membrane (TM) 30, via one or more temporarily implanted tympanic membrane port devices 200. Distal end portions of the instruments 110 are thereby advanced into the middle ear 40 toward a round window 52 of the cochlea 50.

As described in more detail below, the instruments of the system can be configured to achieve a targeted delivery of the formulation or implant 100 into the round window niche 52 and adjacent to the round window membrane of the cochlea 50. The active ingredient of the formulation or implant 100 then moves passively by diffusion across the membrane of the round window 52, according to a concentration gradient, and into the perilymph (within the cochlea 50). In some embodiments, the formulation or implant 100 that is delivered adjacent to the round window membrane of the cochlea 50 can thereafter reside adjacent to or within the niche of the round window 52 as a semisolid gel substance. As a gel substance, the delivery of the formulation or implant 100 will remain in the targeted site at the cochlea 50 so that the formulation or implant 100 can gradually release its active ingredient for an extended period of time such as days, weeks, or even months.

After the delivery of the formulation or implant 100, the instruments 110 and the one or more TM port device(s) 200 can be removed from the patient 10. The TM port device(s) 200 can be sized and shaped so that the openings of the TM 30 (in which the TM port device(s) 200 were positioned) can naturally heal (without suturing). The formulation or implant 100 (e.g., in gel form) will remain at the targeted site in the cochlea 50 to provide extended therapeutic effects by a controlled, sustained release of the active ingredient into the body of the patient 10.

Sustained release can encompass the release of effective amounts of an active ingredient of the formulation or implant 100 for an extended period of time. The sustained release may encompass first order release of the active ingredient, zero order release of the active ingredient, or other kinetics of release such as intermediate to zero order and first order, or combinations thereof. The sustained release may also encompass controlled release of the active ingredient of the formulation or implant 100 via passive molecular diffusion driven by a concentration gradient across a membrane or porous structure.

The procedure for delivering the formulation or implant 100 into the cochlea 50 of the patient 10 can be repeated periodically as needed for a particular patient's treatment. For example, in some cases deliveries of the formulation or implant 100 can be administered about every three to 24 months, each time using a new TM port device(s) 200 and delivery instruments as described herein. In particular cases, an assessment of the patient 10 can be performed to determine whether or when to administer more formulation or implant 100. In some cases, a procedure such as magnetic resonance imaging (MRI) (or other type of procedure) can be performed to help make such an assessment.

Referring also to FIGS. 3-7, an example system (or kit) of devices and instruments that can be used to perform the procedure to treat hearing loss and other ear disorders as described herein can include, but is not limited to, one or more of the following: (i) a TM port insertor 220, (ii) one or more TM port devices 200, (iii) an endoscope 300 (or other direct visualization instrument) sized to fit through the TM port device 200, (iv) a forceps 400 (or other type of tissue manipulator device as described further below) sized to fit through the TM port device 200, and (v) an injector instrument 800 that is sized to fit through the TM port device 200 and (optionally) includes a steerable distal tip.

The endoscope 300, the forceps 400, and the injector instrument 800 are configured to access the middle ear 40 through the TM port devices 200 while each TM port device 200 is temporarily implanted in the TM 30 of the patient 10. That is, at least the distal end portions of each of the endoscope 300, the forceps 400, and the injector instrument 800 are configured to slidably pass through a lumen 202 defined by the TM port device 200 while the TM port device 200 is removably implanted in the TM 30. In cases that the endoscope 300, injector instrument 800, or any other instruments are of differing diameters or outer profiles, the TM port devices 200 can be of different sizes or shapes that accommodate correspondingly. In some embodiments as described further below, the endoscope 300 (while its distal end portion is positioned in the middle ear 40) is used by the clinician 1 to obtain direct visualization as the clinician 1 manipulates another instrument, such as the forceps 400 or injector instrument 800, in the middle ear 40 to perform the treatment for hearing loss and other ear disorders as described herein. The injector instrument 800 can be adapted to deliver a formulation and/or an implant.

During use, the proximal end portions of each of the depicted instruments remain external to the patient 10, and operable/controllable by the clinician 1. Each of the instruments, the TM port device 200, and the formulation or implant 100 are described further below.

Referring also to FIG. 8, the patient 10 is depicted in an example suitable position and orientation to receive the procedure(s) to treat hearing loss and other ear disorders as described herein. In some cases, the procedure can be performed with the patient 10 fully supine (as shown) or reclined in a chair.

The head of the patient 10 can be rotated to between about 30 to 45 degrees away from the clinician 1 (toward the opposite ear of the patient 10). The jaw of the patient 10 can be slightly elevated, and/or the external portion of the ear of the patient 10 may be pulled superiorly and backward to adjust the canal aperture and angularity. As such, the round window 52 of the patient will be oriented generally upward (e.g., away from the ground) so that, upon dispensation of the formulation or implant 100 from the delivery instrument, the formulation or implant 100 is able to pool at the round window 52 and not flow toward the eustascian tube or the ossicular chain.

In some implementations, the patient 10 remains awake during the procedure. That is, the procedure can be performed using a local anesthetic rather than a general anesthetic. For example, in some cases agents such as phenol or lidocaine can be applied to the TM 30 as a local anesthetic to facilitate the procedure. In some cases, the patient can be given general anesthesia for the procedure.

Figure 9:
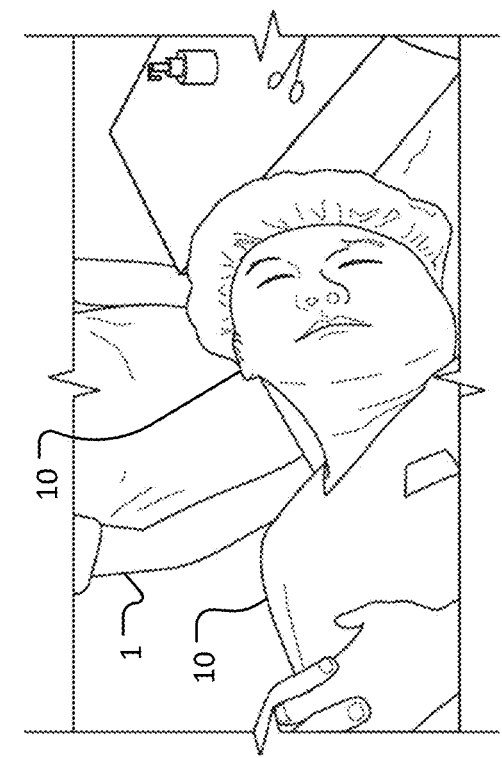
FIG. 9 shows the advancement of a sheath into the patient's outer ear toward the patient's tympanic membrane.

Referring to FIG. 9, after prepping the patient 10 for the procedure, the TM port insertor 220 can be advanced into the outer ear canal 20 toward the TM 30 as part of the procedure of temporarily implanting a TM port device 200 in the TM 30. In some cases, an endoscope (not shown) is used in the outer ear canal 20 to provide direct visualization of the TM port insertor 220 as it is advanced and used to insert a TM port device 200 in the TM 30. In some cases, a surgical microscope or other magnifying instrument is used to provide direct visualization of the TM port insertor 220 as it is advanced and used to temporarily implant the TM port device 200 in the TM 30.

Referring to also to FIGS. 12-15, the example TM port insertor 220 includes an elongate delivery sheath 222, a pusher catheter 224, and a trocar needle 226. The pusher catheter 224 is slidably disposed within a lumen defined by the delivery sheath 222. The trocar needle 226 is slidably disposed within a lumen defined by the pusher catheter 224. In particular embodiments, the pusher catheter 224 and the trocar needle 226 are combined together as a single instrument.

When a TM port device 200 is operatively loaded onto the TM port insertor 220 (e.g., FIG. 13), the TM port device 200 is releasably coupled with the trocar needle 226, abutted against a distal end of the pusher catheter 224, and slidably disposable within the lumen of the delivery sheath 222. That is, at least a distal end portion of the trocar needle 226 is slidably disposed within the lumen 202 of the TM port device 200. In some embodiments, a clearance fit is used between the outer diameter of the distal end portion of the trocar needle 226 and the inner diameter of the lumen 202 of the TM port device 200. In particular embodiments, a slight interference fit is used between the outer diameter of the distal end portion of the trocar needle 226 and the inner diameter of the lumen 202 of the TM port device 200.

While the TM port device 200 is coupled with the trocar needle 226, the distal end face of the pusher catheter 224 is (or can be) abutted against the proximal end face of the TM port device 200. Accordingly, the pusher catheter 224 can apply a distally directed force against the TM port device 200 during the uncoupling, or to uncouple, the TM port device 200 from the trocar needle 226 (and from the TM port insertor 220 as a whole). Said simply, the pusher catheter 224 can be used to push distally the TM port device 200 off the trocar needle 226. Or, said another way, the pusher catheter 224 can counteract proximally directed force from the TM port device 200 as the trocar needle 226 is pulled proximally out of the lumen 202 of the TM port device 200.

The TM port device 200 is slidably disposable within the lumen of the delivery sheath 222. That is, the TM port device 200 can be removably contained within the lumen of the delivery sheath 222 (as in FIG. 12, in which the TM port device 200 is not visible because it is located inside of the delivery sheath 222). This arrangement can be used, for example, during advancement within the outer ear canal 20 of the TM port insertor 220 loaded with a TM port device 200 as depicted in FIG. 9.

The example TM port device 200 includes three conjoined, contiguous portions: (i) a distal end portion 204, (ii) a middle portion 206, and (iii) a proximal end portion 208. The lumen 202 runs centrally through each of the portions 204/206/208. In some embodiments, the lumen 202 has a diameter in a range of 0.4 mm to 0.6 mm, 0.5 mm to 0.75 mm, or 0.5 mm to 1.0 mm, without limitation.

The inner diameter or lumen of the proximal portion 208 can be tapered to have a larger diameter at the proximal end, creating a funnel shape to facilitate the alignment of instruments as they enter the port device.

The shape of the distal end portion 204 can be frustoconical. That is, the distal-most end of the distal end portion 204 has a smaller outer diameter than the proximal-most end of the distal end portion 204. The middle portion 206 and the proximal end portion 208 are each cylindrical. The outer diameter of the middle portion 206 is smaller than the outer diameters of each of: (i) the proximal-most end of the distal end portion 204 and (ii) the proximal end portion 208. Accordingly, the middle portion 206 can be considered a "waist region" of the TM port device 200 in this embodiment. The lumen 202 can be conical, cylindrical, oblong, pyramidal, or other shapes, as can the distal end portion 204.

As described further below, the middle portion 206 is where the tissue of the TM 30 will reside (at least primarily) while the TM port device 200 is implanted in the TM 30. The relatively smaller outer diameter of the middle portion 206 (as compared to the outer diameters of adjacent portions of the distal end portion 204 and the proximal end portion 208) will facilitate detainment of the TM port device 200 in the TM 30. In some embodiments, the outer diameter of the middle portion 206 is in a range of 0.25 mm to mm, 0.25 mm to 1.0 mm, or 0.5 mm to 1.25 mm, without limitation. The longitudinal length of the middle portion 206 can be in a range of 0.1 mm to 0.3 mm, 0.1 mm to 0.5 mm, or 0.2 mm to 0.6 mm, without limitation. The outer diameter and length of the middle portion 206 is sufficient to receive the thickness of the TM 30 while preventing buckling, tearing, or other forces from being imparted inadvertently on the TM 30 upon insertion of the TM port device 200. In some embodiments, no waist region is included, and frictional fit between the distal section and TM is sufficient to hold the port device in the TM for the duration of a procedure while reducing forces TM is exposed to during port insertion or removal.

In some embodiments, the TM port device 200 can be implanted in the TM 30 without the use of a trocar needle. Instead, an incision in the TM 30 can be made first using a blade, needle, or laser. Then, the TM port device 200 can be implanted in the TM 30 by advancing the TM port device 200 into the incision.

While the TM port device 200 is implanted (or attached, coupled, engaged, etc.), to the TM 30, the TM port device 200 performs as a grommet, a stress relief member to prevent tearing of the TM 30, a middle ear access port, an instrument insertion tunnel, a working channel, and the like.

The TM port device 200 is configured and sized so that its removal from the TM 30 does not necessitate the use of sutures to seal the incision or fenestration formed in the TM 30 during insertion of the TM port device 200. Generally, a self-sealing fenestration through the TM 30 is no greater than about 2.5 mm in length, preferably between about 0.5 mm and 1.5 mm in length. Although the tools and methods described herein provide the advantage of suture-less access to the middle and/or inner ear, this does not preclude a surgeon from applying one or more closure techniques upon removal of the TM port device 200. That is, if the clinician 1 so desires, one or more techniques for closure of the fenestration(s) in the TM 30 can be performed.

The TM port device 200 can be formed of a material having a rigidity and strength to be inserted and removed from the TM 30 while also withstanding stresses that may arise during manipulation of surgical instruments inserted therethrough. In some embodiments, at least a portion of the TM port device 200 is formed of surgical metals such as stainless steel, titanium, platinum, Nitinol, and/or plastics such as polyimide, PEEK, fluoropolymers, silicone, and the like. In some embodiments, the inserted portion of the TM port device 200 can be formed of polyimide (or other rigid or semi-rigid polymers) and have a maximum outer diameter of no more than about 20 gauge (0.8 mm). One or more portions of the TM port device 200 can be coated with, or formed of, a resilient conformable material. For example, the retention feature 102 can be coated with or formed by over-molding with a material such as silicone or polyurethane.

Still referring to FIG. 9, in preparation for implanting the TM port device 200 in the TM 30, the TM port insertor 220 internally loaded with a TM port device 200 is advanced in the outer ear canal 20 toward the TM 30. During the advancement, the TM port insertor 220 can be configured as in FIG. 12, wherein the pusher catheter 224, the trocar needle 226, and the TM port device 200 are all within the lumen of the delivery sheath 222.

Figure 10:
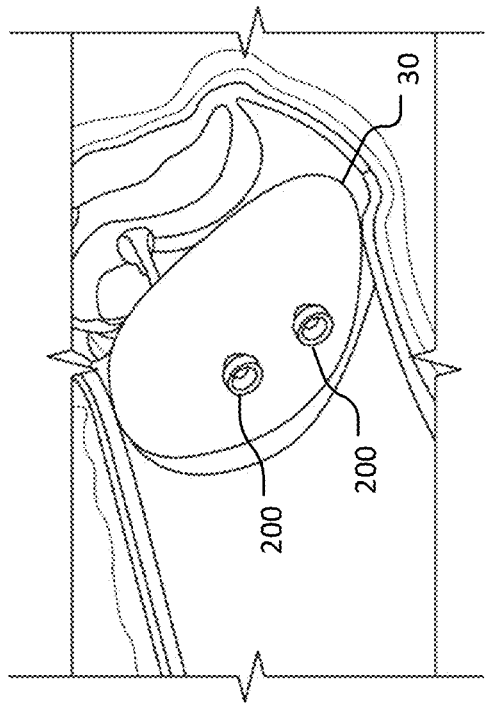
FIG. 10 shows the puncture of the patient's tympanic membrane and placement of a tympanic membrane port device in the patient's tympanic membrane.
Figure 13:
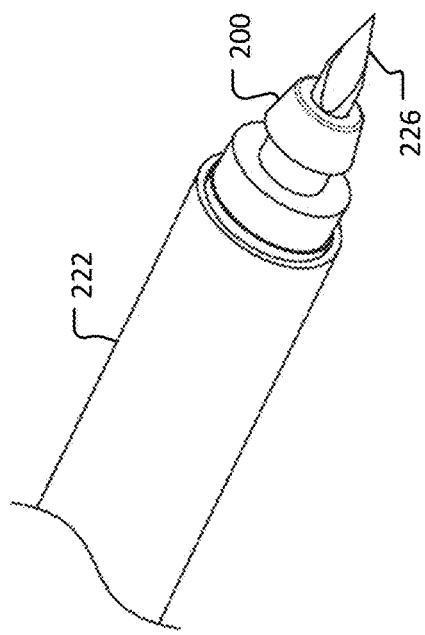
FIG. 13 shows a perspective view of the sheath of FIG. 12 with a tympanic membrane port device and a delivery trocar extending distally from the sheath.
Figure 15:
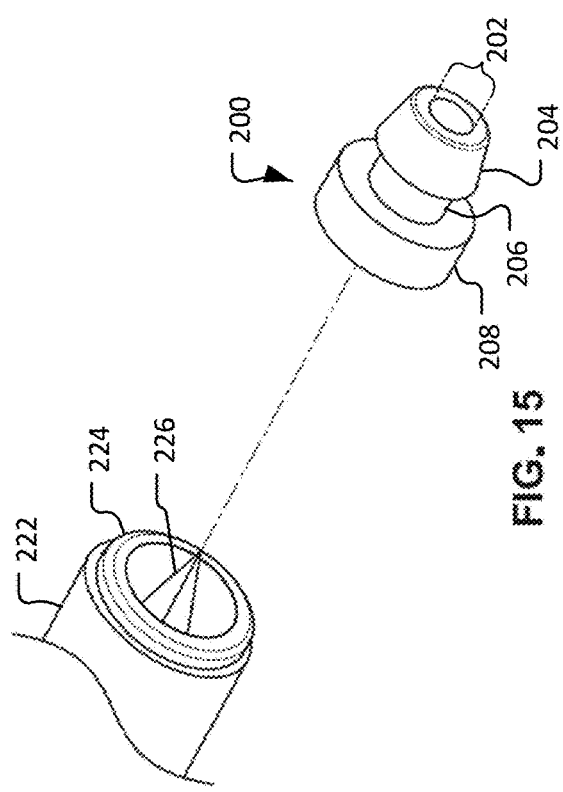
FIG. 15 shows a perspective view of the tympanic membrane port device of FIG. 13 separated from the sheath and delivery trocar.
Figure 12:
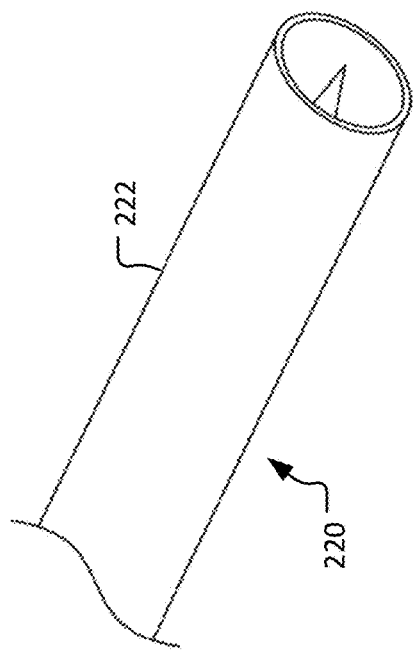
FIG. 12 shows a perspective view of a sheath that delivers a tympanic membrane port device.
Figure 14:
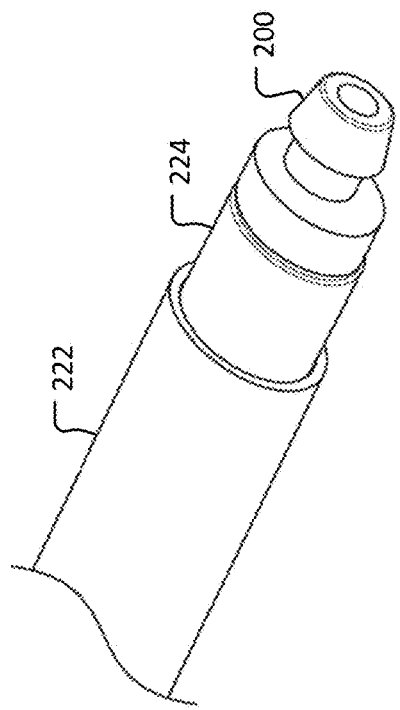
FIG. 14 shows a perspective view of the devices of FIG. 13 with the needle of the delivery trocar withdrawn proximally.

Referring to FIG. 10, when the delivery sheath 222 has been advanced within the outer ear canal 20 to the extent that the distal end of the delivery sheath 222 is adjacent to the TM 30, the pusher catheter 224, the trocar needle 226, and the TM port device 200 can then be extended distally out from the interior of the delivery sheath 222 (as also depicted in FIG. 13). Since the distal tip portion of the trocar needle 226 is a beveled, sharp tip that is configured for puncturing the TM 30, the distal tip portion of the trocar needle 226 can be made to puncture the TM 30. As the pusher catheter 224 (and optionally the trocar needle 226) is extended farther distally, the distal end portion 204 (FIG. 15) of the TM port device 200 will enter and enlarge (dilate) the puncture of the TM 30 initially created by the trocar needle 226. Still farther advancement will position the middle portion 206 of the TM port device 200 in detained engagement with the TM 30. Then, as depicted in FIG. 15, the TM port insertor 220 can be withdrawn from the TM port device 200, leaving the TM port device 200 releasably coupled with the TM 30.

Figure 11:
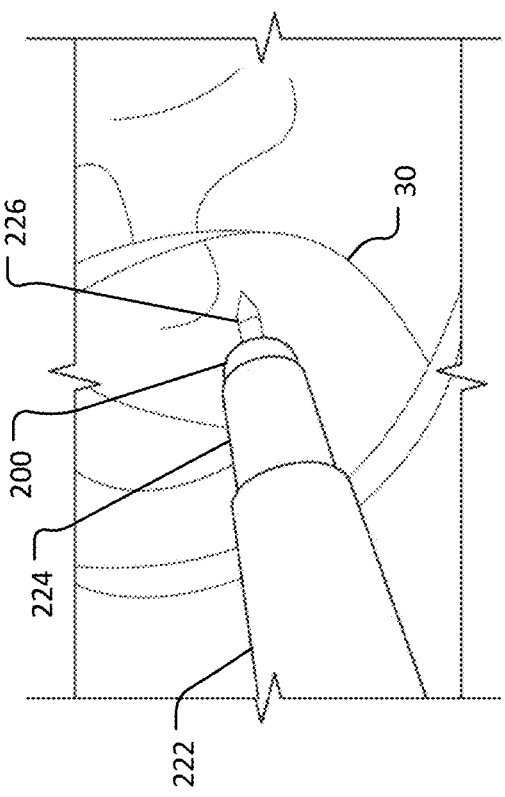
FIG. 11 shows two tympanic membrane port devices positioned in the patient's tympanic membrane.

Referring to FIG. 11, one or more of the TM port devices 200 can be temporarily/removably implanted in the TM 30. While implanted, the proximal end portions 208 of the TM port devices 200 are located in the outer ear canal 20, the distal end portions 204 of the TM port devices 200 are located in the middle ear 40, and the middle portions 206 of the TM port devices 200 receive the tissue of the TM 30.

While implanted, the lumens 202 of the TM port devices 200 define open passageways between the outer ear canal 20 and the middle ear 40. In some embodiments, the passageways of the TM port devices 200 between the outer canal and middle ear can contain frictional elements, valves, or other elements to adjust the movement of instruments, gases, or liquids through passageways of the TM port devices 200.

As depicted, in some embodiments two of the TM port devices 200 are temporarily implanted in the TM 30. In such a case, the two TM port devices 200 can be laterally spaced apart from each other while implanted in the TM 30 (e.g., laterally with respect to the axes defined by the passageways of the TM port devices 200). In some embodiments, the two TM port devices 200 are laterally spaced apart from each other, while implanted in the TM 30, by a distance in a range of 0.5 mm to 8 mm.

Figure 16:
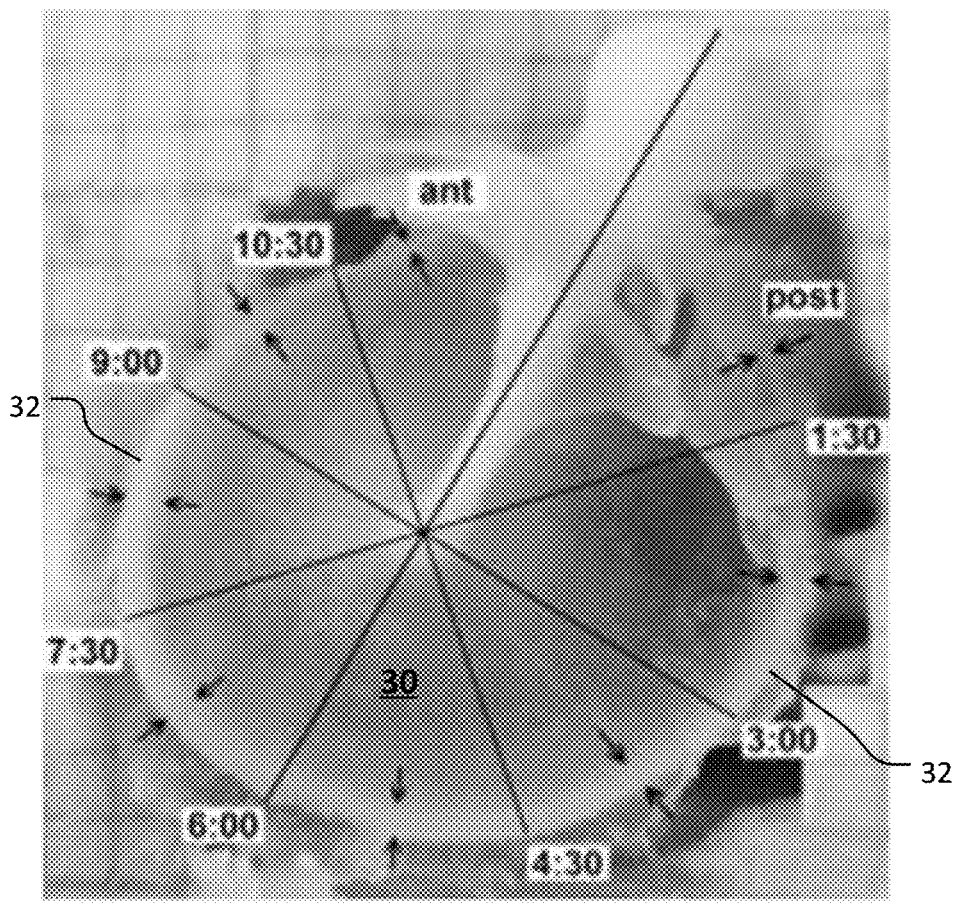
FIG. 16 illustrates a right tympanic membrane with overlaid lines and markings that indicate coordinates of locations around the tympanic annulus surrounding the tympanic membrane.

FIG. 16 illustrates a right TM 30 with overlaid lines and markings that indicate coordinates of locations around the tympanic annulus 32 surrounding the tympanic membrane 30. Locations on the tympanic annulus 32 can be identified using a clock face analogy with the malleus located at 12 o'clock, as shown.

The TM 30 is a thin, cone-shaped membrane that separates the external ear from the middle ear. The tympanic annulus 32 is a thicker fibrocartilaginous ring peripherally surrounding the TM 30. Accordingly, the tympanic annulus 32 provides a strong, stable tissue in which to anchor TM port devices.

Figure 17:
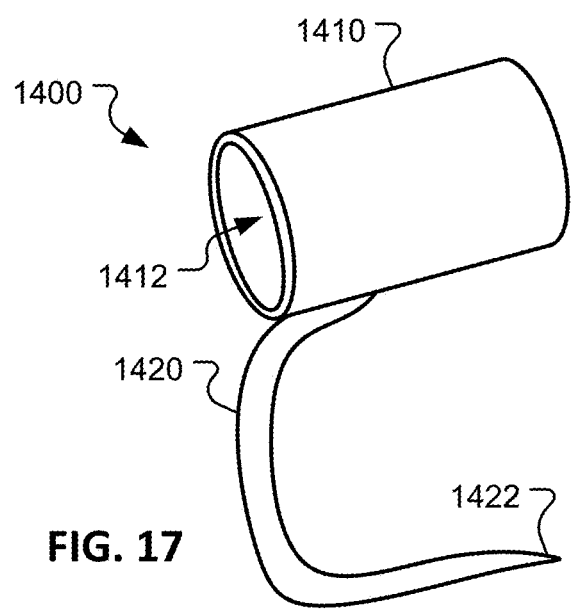
FIG. 17 shows an example tympanic membrane port device that includes an anchor portion.

FIG. 17 shows another example TM port device 1400. The TM port device 1400 includes a laterally extending anchor portion 1420 attached to a cannula 1410. The cannula 1410 defines a port 1412 that serves as a passageway for instruments described herein. Such a laterally extending anchor portion 1420 can be optionally included on any of the TM port devices described herein.

As described further below, the cannula 1410 can be situated (implanted during the procedure and then removed) in the TM 30 (such that instruments can pass through the TM 30 via the port 1412 during the procedure) while the anchor portion 1420 is positioned in the tympanic annulus 32. In this manner, the strong tympanic annulus 32 can serve as a stable foundation to anchor the port device 1400. Accordingly, the anchor portion 1420 transfers stresses to the tympanic annulus 32 such that stresses to the TM 30 itself are minimized when instruments are used in the port 1412.

The anchor portion 1420 has a sharp, pointed tip 1422. The tip 1422 can pierce through the tympanic annulus 32 when the tympanic membrane port device 1400 is implanted in the TM 30 and the tympanic annulus 32. The lateral length of the anchor portion 1420 can be made to any desired length. The length of the anchor portion 1420 will help to define the resulting position of the cannula 1410 in the TM 30.

While the cannula 1410 is depicted as having a cylindrical outer profile, the cannula 1410 is not limited to such an outer shape. For example, in some embodiments the outer profile of the cannula 1410 can be as shown in FIG. 15 (e.g., TM port device 200) and elsewhere herein. In some embodiments, the outer profile of the cannula 1410, or portions thereof, can be frustoconical, hourglass shaped, arcuate, and so on. The port 1412 can also have various cross-sectional shapes. For example, in some embodiments the port 1412 is curved, rather than linear as shown.

Figure 18:
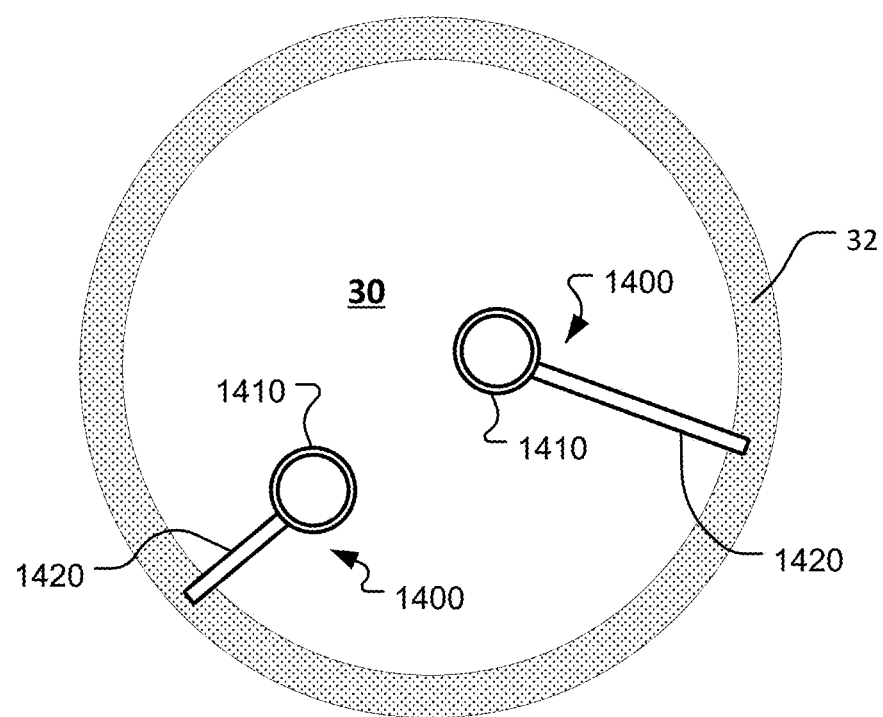
FIG. 18 shows a tympanic membrane and tympanic annulus with two tympanic membrane port devices of FIG. 50.

FIG. 18 shows a tympanic membrane 30 and tympanic annulus 32 with two tympanic membrane port devices 1400 implanted therein. It can be seen that the cannulae 1410 are positioned to provide a passageway through the TM 30, while the anchor portions 1420 extend to, and penetrate through, the tympanic annulus 32. Accordingly, the tympanic annulus 32 provides a strong, stable anchoring for the tympanic membrane port devices 1400.

It can be envisioned that the anchor portions 1420 could be used to attach or pierce other members, such as an elastomeric or hydrogel ring positioned overlaying the tympanic annulus 32. The elastomeric ring could be squeezed down the ear canal and placed at the tympanic membrane such that it expands back to shape at the periphery of the membrane overlaying the tympanic annulus, This removable member could then obviate the need for piercing or attaching directly to the tympanic annulus (and potential pain associated with that step) while still enabling stabilization and anchoring of the ports 1410.

Figure 19:
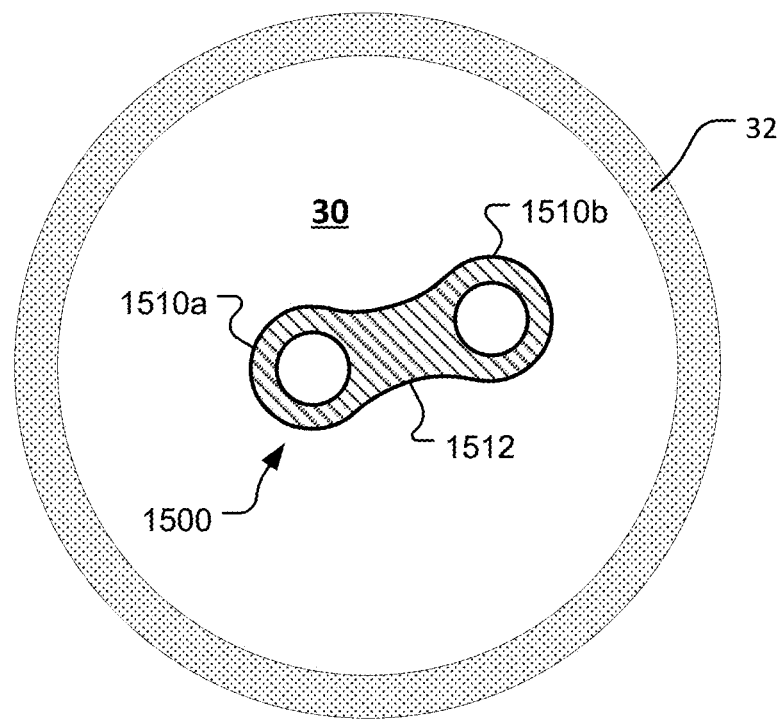
FIG. 19 shows a tympanic membrane and tympanic annulus with an example dual tympanic membrane port device.

FIG. 19 shows a tympanic membrane 30 and tympanic annulus 32 with an implanted example dual tympanic membrane port device 1500. The dual tympanic membrane port device 1500 includes a first tympanic membrane port device 1510a and a second tympanic membrane port device 1510b. Accordingly, two ports through the TM 30 are provided by the dual tympanic membrane port device 1500.

The tympanic membrane port devices 1510a and 1510b are connected to each other by a joining member 1512. The joining member 1512 can be any desired length to establish the center-to-center distance between the two tympanic membrane port devices 1510a and 1510b.

Figure 20:
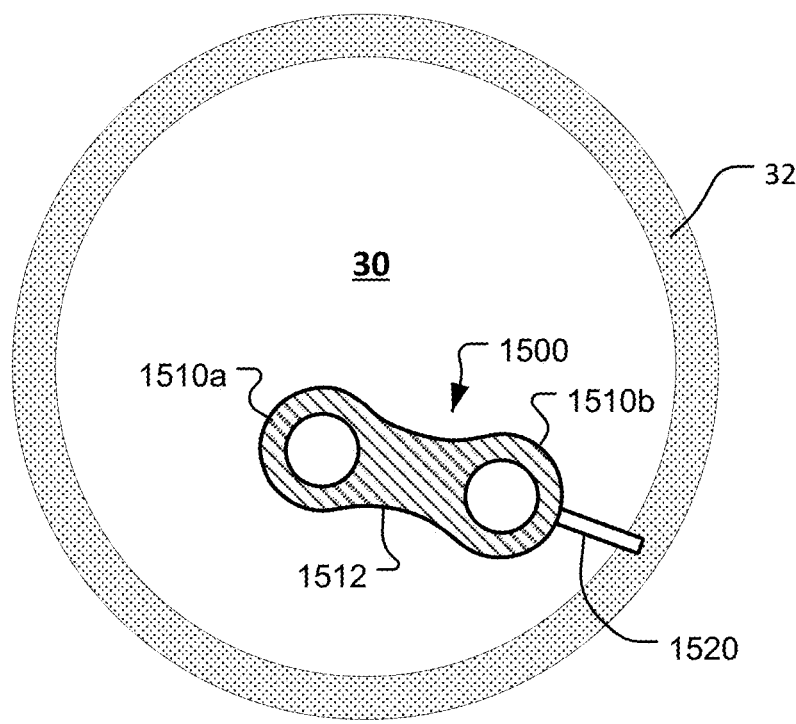
FIG. 20 shows a tympanic membrane and tympanic annulus with another example dual tympanic membrane port device.

FIG. 20 shows a tympanic membrane 30 and tympanic annulus 32 with another implanted example dual tympanic membrane port device 1500. In this example, the tympanic membrane port device 1500 includes an anchor portion 1520. The anchor portion 1520 laterally extends from the tympanic membrane port device 1510b and is pierced through the tympanic annulus 32 (e.g., as described above in reference to the anchor portion 1420 of the tympanic membrane port device 1400; FIGS. 17 and 18). It should be understood that the anchor portion 1520 can laterally extend in any desired direction from the dual tympanic membrane port device 1500. While the depicted dual tympanic membrane port device 1500 includes a single anchor portion 1520, in some embodiments two or more of the anchor portions 1520 can be attached to the dual tympanic membrane port device 1500. Accordingly, in some embodiments the dual tympanic membrane port device 1500 can be anchored at two or more locations of the tympanic annulus 32 (in addition to passing through the TM 30 at two locations).

Figure 21:
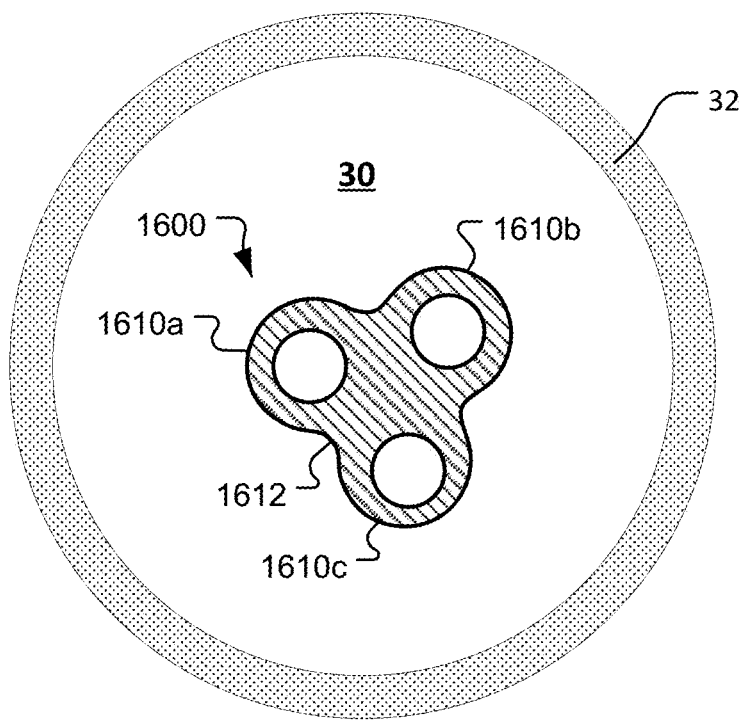
FIG. 21 shows a tympanic membrane and tympanic annulus with an example triple tympanic membrane port device.

FIG. 21 shows a tympanic membrane 30 and tympanic annulus 32 with an example triple tympanic membrane port device 1600. The triple tympanic membrane port device 1600 includes a first tympanic membrane port device 1610a, a second tympanic membrane port device 1610b, and a third tympanic membrane port device 1610c. Each of the tympanic membrane port devices 1610a-c defines a port through the TM 30.

The tympanic membrane port devices 1610a-c are interconnected via a joining member 1612. The joining member 1612 can be any desired shape and length to establish the center-to-center distances between the three tympanic membrane port devices 1610a-c. In some embodiments, one or more anchor portions (e.g., like the anchor portion 1520; FIG. 20) can be attached to the triple tympanic membrane port device 1600 to facilitate anchoring of the triple tympanic membrane port device 1600 in the tympanic annulus 32.

In some cases, the third port device could instead be a lens to allow trans-tympanic membrane viewing of the middle ear through the operating microscope. This would obviate the need for an endoscope and free a surgeon's hand and allow for binocular visualization. This lens could be convex to allow for widefield viewing not otherwise possible with the external microscope alone.

Figure 22:
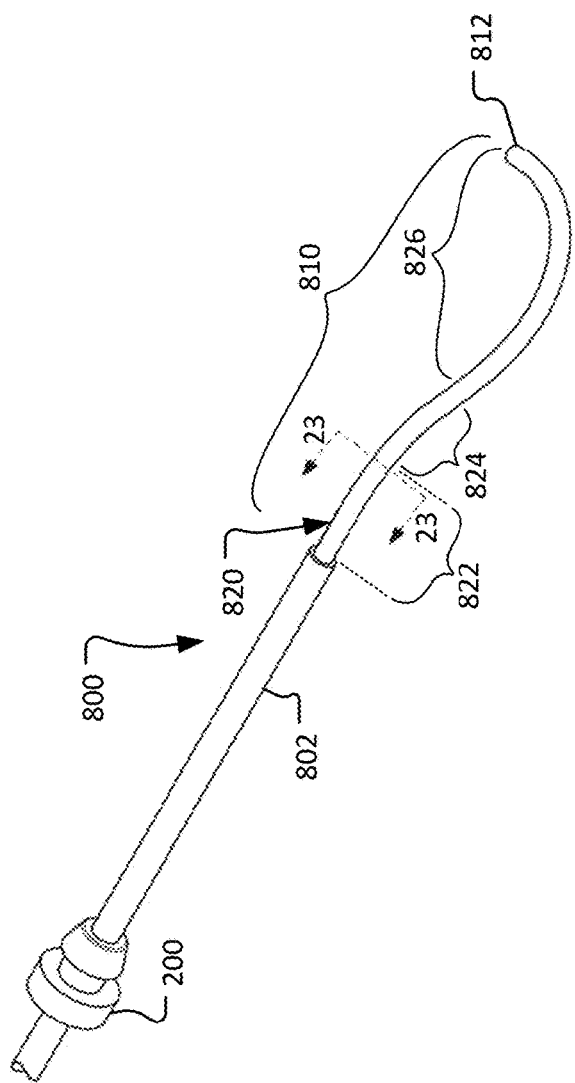
FIG. 22 shows another example injection device extending through an example tympanic membrane port device.

Referring to FIG. 22, the example injector instrument 800 is shown here in more detail. The injector instrument 800 can be adapted to deliver a formulation or an implant device that delivers a formulation.

In the depicted embodiment, the injector instrument 800 includes a sheath 802 and an injection tube 820. The injection tube 820 is slidable within a lumen defined by the sheath 802. That is, the injection tube 820 can be selectively extended distally, by the clinician 1, from the distal end of the sheath 802 as depicted here. In addition, the injection tube 820 can be selectively withdrawn proximally, by the clinician 1, into the sheath 802 so that the injection tube 820 does not extend beyond the distal end of the sheath 802. When the injection tube 820 is extended (as shown), the exposed portion of the injection tube 820 makes up the distal end portion 810 of the injector instrument 800. The distal end portion 810 terminates at a distal tip 812 that defines a port through which the therapeutic agent, or medicament, is ejected.

The portion of the injection tube 820 that makes up the distal end portion 810 of the injector instrument 800 can have various shapes and form factors. For example, in the depicted example, the exposed injection tube 820 includes a linear portion 822, a first curved portion 824, and a second curved portion 826. The curved portions 824 and 826 become linear, however, when the injection tube 820 is constrained within the sheath 802. Alternatively, the curved portions 824 and 826 take on the shape of the lumen of the injection tube 820 if the lumen is not linear.

It can be said that the curved portions 824 and 826 have shape memory. That is, when the clinician 1 extends the curved portions 824 and 826 from the confines of the sheath 802, the curved portions 824 and 826 will revert to exhibiting curved shapes as shown.

In particular embodiments, the combination of the first and second curved portions 824 and 826 define an "S-shape" for the distal end portion 810 of the injector instrument 800. The S-shape is formed because the first curved portion 824 curves in an opposite direction in comparison to the curve of the second curved portion 826. Said another way, the center point of the radius of curvature of the first curved portion 824 is on an opposite side of the injection tube 820 as compared to the center point of the radius of curvature of the second curved portion 826. It should be understood that this shape of the injection tube 820 with the linear portion 822, the first curved portion 824, and the second curved portion 826 is just one example of a type of shape that the injection tube 820 can have. Other shapes are also envisioned and within the scope of this disclosure (such as, but not limited to, the shape shown in FIGS. 38-40 as described below).

It can be envisioned that as the clinician 1 begins to extend the injection tube 820 distally out from the distal end of the sheath 802, the second curved portion 826 will emerge first. Accordingly, the distal end portion 810 will initially have a single curve (as exhibited by the second curved portion 826). If the clinician 1 continues extending the injection tube 820 distally out from the distal end of the sheath 802, eventually the first curved portion 824 will begin to emerge. As the first curved portion 824 emerges, it can be envisioned that the entire distal end portion 810 will be correspondingly deflected in the opposite direction of the second curved portion 826.

As the injection tube 820 is extended out from the distal end of the sheath 802 to various extents, the distal tip 812 will be moved into various positions because of the shape memories of the first and second curved portions 824 and 826. Accordingly, the distal tip 812 is controllably positionable by the clinician 1 by controlling the extent to which injection tube 820 is extended out from the distal end of the sheath 802 and using the axial rotation of the instrument 800. Said another way, the clinician 1 can steer the distal end portion 810, and the distal tip 812 in particular, by controlling the extent to which injection tube 820 is extended out from the distal end of the sheath 802. This functionality can be used by the clinician 1 to position accurately the distal tip 812 in the round window 52 in preparation for injecting the therapeutic agent therefrom.

While the distal end portion 810 includes the first and second curved portions 824 and 826 that are curved in the same plane but in opposite directions, in some embodiments the distal end portion 810 can include two or more curved portions that are in differing planes.

Figure 23:
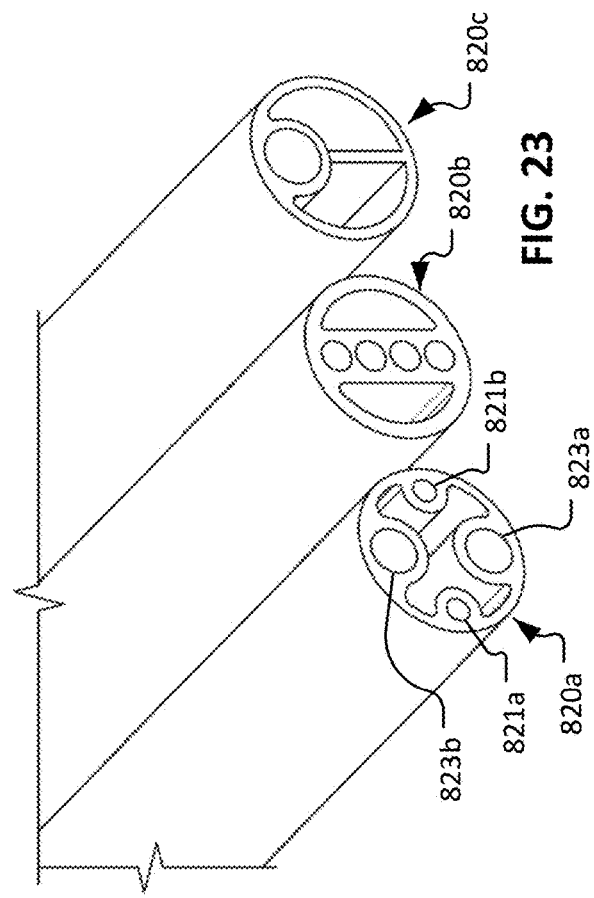
FIG. 23 show example cross-sections of an extendable injection tube of the injection device of FIG. 22.

In some embodiments, the shape of the distal end portion 810 can be selectively controlled by the clinician 1 using control members that are located within lumens defined within the wall of the injection tube 820. For example, FIG. 23 shows some example cross-sections (as taken along break line 23-23 in FIG. 22) of various types of tube configurations that the injection tube 820 can be made from. It can be seen, for example, that the tube 820a includes a first pair of lumens 821a and 821b that are 180° opposed to each other. In some embodiments, such lumens 821a-b can house control wires that are anchored, for example, near the distal tip 812. Accordingly, when the clinician 1 pulls proximally on one of the wires and relaxes the tension on the other opposed one of the wires, the distal end portion 810 will deflect in the direction of the tensioned wire. In this manner, the clinician 1 can steer the distal end portion 810 as desired.

Further, the example tube 820a also includes a second pair of lumens 823a and 823b. These lumens 823a-b define a plane that is perpendicular to the plane defined by the first pair of lumens 821a-b. Again, the second pair of lumens 823a-b can house control wires that are anchored, for example, near the distal tip 812. Accordingly, when the clinician 1 pulls proximally on one of the wires and relaxes the tension on the other opposed one of the wires, the distal end portion 810 will deflect in the direction of the tensioned wire.

If all four of the lumens 821a-b and 823a-b house such control wires, it can be envisioned that the clinician 1 can control the orientation, or steer, the distal end portion 810 to extend in any direction and to have any orientation as desired. Moreover, this can be true in either case of when the distal end portion 810 has shape memory that includes one or more curves (e.g., as depicted in FIG. 41) or when the distal end portion 810 is naturally linear.

While the example tube 820a has a particular arrangement of lumens 821a-b and 823a-b, the other example tubes 820b and 820c have other arrangements of lumens. Accordingly, tubes 820b and 820c, or tubes with any other arrangements of lumens, can also be used in accordance with the concepts described in the example context of the tube 820a.

In some embodiments, the lumens in the wall of the injection tube, such as the lumens 821a-b and 823a-b of the injection tube 820a, can house control members that are stiffening elements. Such stiffening elements can also be used to controllably deflect or steer the distal end portion 810. For example, in some embodiments the injection tube 820 naturally has one or more curves (e.g., the first curved portion 824 and the second curved portion 826). When stiffening elements (e.g., strong, bend-resistant linear shafts) are moved distally through the lumens in the wall of the injection tube 820 and into the regions of the curves, the curves will tend to straighten out. Conversely, when such stiffening elements are pulled proximally out from the regions of the curves, the curves will again reform. In such a manner using stiffening elements in the wall of the injection tube 820, the clinician 1 can control the orientation, or steer, the distal end portion 810 to extend in any direction and to have any orientation as desired. Conversely, in some embodiments the stiffening elements can have pre-formed curves (e.g., biased laser cut wires or hypotubes, shape memory elements or wires, or hypotubes made of materials such as nitinol) while the injection tube 820 is generally straight. Such stiffening members could be pushed distally relative to the relatively inflexible access shaft such that the stiffening member's curve imparts a curve to the injection tube's distal tip. It can be envisioned that stiffening elements with differing degrees of preset curves could be switched out to adjust curvature while allowing the injection tube 820 to remain in place and thereby limit potential disturbance of the TM 30. In another embodiment, the stiffening member can be a shape memory element (such as nitinol) that will take on its curve once exposed to elevated temperatures, such as those within the patient. In other embodiments, the elevated temperature could be greater than the patient's internal temperature. In such a case, the elevated temperature can be reached by applying voltage to the nitinol element, by exposure to heat generated by the light source, or by another technique for heating the nitinol element.

Figure 24:
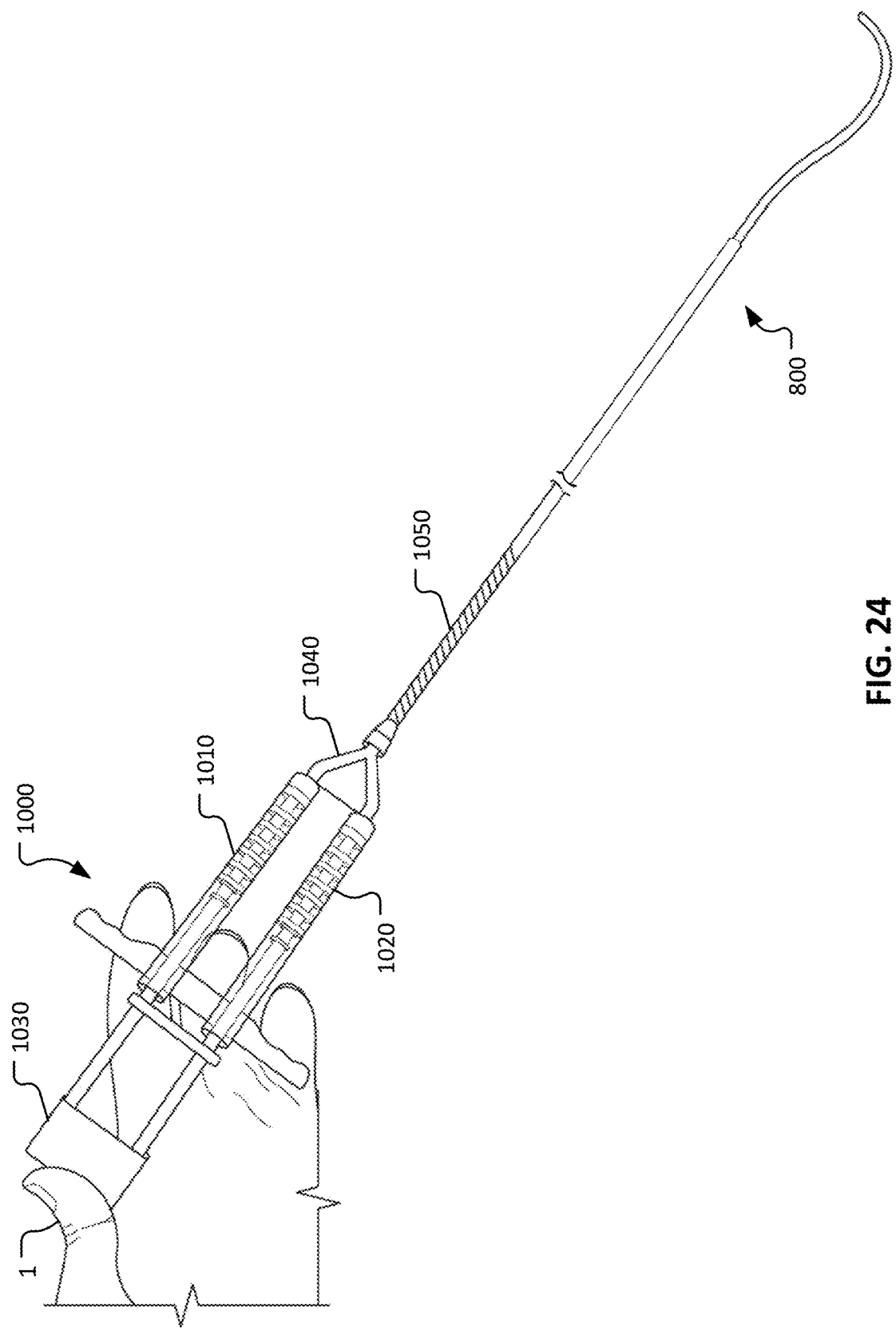
FIG. 24 shows an example therapeutic agent supply device coupled to an example injection device.

Referring to FIG. 24, in some embodiments, the formulation 100 starts to become a gel substance when two liquid components are mixed together, such as by an example dual syringe 1000. The dual syringe 1000 mixes the two liquid components during the injection so that the two liquid components mix just prior to the delivery. The gelation reaction time between the two liquid components causes the homogeneous mixture of two liquid components to become a gel consistency rapidly, in keeping with the design of the dual syringe 1000.

The dual syringe 1000 includes a first barrel 1010, a second barrel 1020, a dual plunger 1030, a Y-connector 1040, and a static mixer 1050. The outlet of the static mixer 1050 is releasably coupled to an injector instrument, such as the injector instrument 800.

The first and second barrels 1010 and 1020 contain the first and second liquid components, respectively, and keep the first and second liquid components separate from each other while the first and second liquid components are in the first and second barrels 1010 and 1020. The dual plunger 1030 includes two plungers (one plunger in each of the first and second barrels 1010 and 1020) that are coupled together so that the displacement of the two plungers by the clinician 1 are synchronized during the injection. The Y-connector 1040 receives the first and second liquid components output from the first and second barrels 1010 and 1020 and directs the first and second liquid components to flow into contact with each other at the outlet of the Y-connector 1040. The static mixer 1050 receives the first and second liquid components from the Y-connector 1040 and causes the first and second liquid components to mix together to create a homogeneous mixture of the first and second liquid components. The homogeneous mixture of the first and second liquid components output from the static mixer 1050 is input into the injector instrument 800 from the homogeneous mixture of the first and second liquid components can be delivered adjacent to the cochlea 50 of the patient 10.

In another embodiment, a single syringe can be used to deliver the formulation or implant 100. In such a case, the gelation time of the formulation components of the formulation or implant 100 are tuned such that the formulation components can be mixed at patient bedside and immediately (before the crosslinking reaction of the formulation components or a majority of the crosslinking reaction takes place) delivered into the cochlea 50 using a standard single syringe attached to the injector instrument. Moreover, in some embodiments photo-crosslinking is used (e.g., FIG. 31). Accordingly, in some embodiments the delivery of the mixed formulation components into the niche of the round window 52 is promptly followed by application of light into the middle ear 40 toward the round window 52 to initiate and/or accelerate the crosslinking, and create the gel consistency of the formulation 100. In some embodiments the gel consistency is generated upon exposure to heat produced by the patient's own body, or by another instrument.

The gel consistency of the formulation 100 causes the formulation 100 to remain adjacent to the round window membrane of the cochlea 50 and to facilitate either short term or sustained release of the active ingredient of the formulation 100. Sustained release can encompass release of effective amounts of the active ingredient of the formulation 100 for an extended period of time. The sustained release may encompass first order release of the active ingredient, zero order release of the active ingredient, or other kinetics of release such as intermediate to zero order and first order, or combinations thereof. The sustained release may encompass controlled release of the formulation 100 via passive molecular diffusion driven by a concentration gradient across a porous structure.

A composition of the formulation 100 can be a mixture. It can be a solution, a suspension, an emulsion, liquid, mist, powder, a paste, aqueous, non-aqueous or any combination of such forms and/or ingredients. A fluid is any composition that can flow. Fluids thus encompass compositions that are in the form of semi-solids, pastes, solutions, aqueous mixtures, gels, lotions, creams and other such compositions.

FIGS. 25-27 show another example injector instrument 900. The injector instrument 900 can be adapted to deliver a formulation and/or an implant device.

In the depicted embodiment, the injector instrument 900 includes a sheath 902 and an injection tube 920. The injection tube 920 is slidable within a lumen defined by the sheath 902. That is, the injection tube 920 can be selectively extended distally, by the clinician 1, from the distal end of the sheath 902 as depicted here in FIGS. 26 and 27. In addition, the injection tube 920 can be selectively withdrawn proximally, by the clinician 1, into the sheath 902 so that the injection tube 920 does not extend beyond the distal end of the sheath 902 as depicted here in FIG. 25. When the injection tube 920 is extended, the exposed portion of the injection tube 920 makes up the distal end portion 910 of the injector instrument 900. The distal end portion 910 terminates at a beveled distal tip 912 that defines a port through which the therapeutic agent, or medicament, is ejected.

The injector instrument 900 can have any of the features that are described above in reference to the injector instrument 800 (including control members), except that the injection tube 920 of the injector instrument 900 has only a single naturally curved portion. Still, the extension direction and orientation of the distal end portion 910 (and of the distal tip 912) is substantially controllable by the clinician 1 by controlling factors such as the length of the distal end portion 910 and the roll, pitch, and yaw of the injector instrument 900 relative to the patient 1.

Referring to FIG. 28, when open access to the niche of the round window 52 has been verified and while the endoscope 300 is slidably disposed through a first one of the TM port devices 200, then the example injector instrument 800 (or any of the injector instruments described herein) can be slidably advanced by the clinician 1 through the second one of the TM port devices 200. A distal end portion 810 of the injector instrument 800 is thereby selectively positionable within the middle ear 40 while being directly visualized using the endoscope 300. The injector instrument 800 will be used, as described below, to deliver the formulation or implant 100 in proximity to the round window 52 (e.g., into the round window niche adjacent to the round window membrane of the cochlea 50 from where the active ingredient of the formulation or implant 100 can move passively by diffusion across the membrane of the round window 52) or other target locations on or in the middle ear and/or inner ear regions of the patient 10.

Referring now to FIG. 29, under the direct visualization of the endoscope 300 (of which the distal end portion 310 is visible here), the clinician 1 can controllably maneuver and orient the distal end portion 810 of the injection tube 820 so that the distal tip 812 is within, or adjacent to, the niche of the round window 52 (or other target location). To do so, the clinician 1 can use any of the techniques described above for deflecting, steering, articulating, extending, and otherwise orientating the distal end portion 810.

Referring also to FIG. 30, when the distal tip 812 is properly positioned in relation to the round window 52 (this being confirmable by the clinician 1 using direct visualization of the endoscope 300), the clinician 1 can then deliver a desired amount the formulation 100 (or an implant) into the round window niche adjacent the round window membrane of the cochlea 50 (or other target location within the middle and/or inner ear region). This delivery can also be performed under direct visualization using the endoscope 300. That is, the clinician 1 can use the endoscope 300 to confirm that the formulation or implant 100 has been delivered to a desired amount and in a desired position. Moreover, the clinician 1 can use the endoscope 300 to monitor, for a period of time, and that the formulation or implant 100 remains in the desired position rather than migrating away from the desired position.

In some embodiments, the delivered formulation 100 will tend to remain in the desired position because the formulation 100 is delivered as, or will become in situ, a gel substance.

Referring to FIG. 31, in some embodiments the formulation 100 can be cured or partially cured (to become a gel substance) in situ just after the formulation 100 is delivered into the cochlea 50. In some such embodiments, light energy (e.g., UV light) to accelerate the curing of the formulation 100 can be applied by the endoscope 300 as depicted, or by another instrument. In other embodiments, the formulation 100 is a thermo-responsive hydrogel that is liquid at room temperature and forms a gel at body temperature. In other embodiments, the formulation is chemically cross-linked at a controlled rate following mixing of two reagents.

Figure 32:
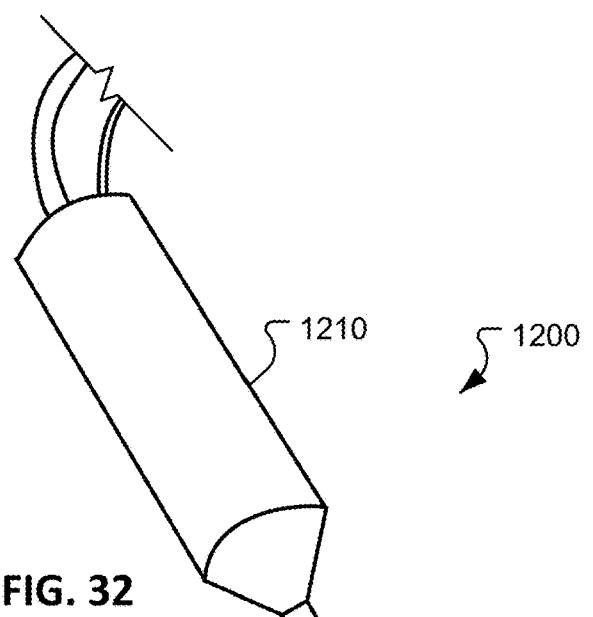
FIG. 32 shows an example otologic instrument with an optional removable sleeve device that defines a working channel coupled to the shaft of the instrument.

FIG. 32 shows an example otologic instrument 1200 that is engaged with an optional removable sleeve device 1300. The sleeve device 1300 defines one or more auxiliary working channels that can receive an additional instrument, as described further below.

The sleeve device 1300 is removably coupled to the shaft 1220 of the instrument 1200. The sleeve device 1300 can have various configurations (as described further below) and can be slidably engaged onto, and removed from, the shaft 1220 of the instrument 1200. The sleeve device 1300 can be made of metal (e.g., stainless steel, titanium, aluminum, etc.) or of a plastic material. In some embodiments, the sleeve device 1300 is transparent.

In the depicted embodiment, the otologic instrument 1200 is an endoscope with a handle 1210. However, the sleeve device 1300 can be used with various other types of otologic instruments as described herein, in addition to the depicted endoscope 1200. In one example arrangement using the sleeve device 1300, the instrument 1200 is an endoscope and an injector device can be extended through an auxiliary working channel defined by the sleeve device 1300. In some such embodiments, a distal tip portion of the injector device can have a natural curve such that the distal tip portion of the injector device can be controllably directed to a location that is non-linear with respect to the longitudinal axis of the auxiliary working channel.

The sleeve device 1300 can have various lengths in relation to the length of the shaft 1220. In some embodiments, the sleeve device 1300 will extend through a TM port device when in use. The bore of the TM port can be made to correspond to the outer profile of the sleeve device 1300 in such a case. Or, the bore of the TM port device can be cylindrical with a diameter that is large enough to accommodate the largest outer size of the sleeve device 1300. In some embodiments, the distal end of the sleeve device 1300 will be located proximal of the TM port device such that the sleeve device 1300 will not extend through the TM port device when in use.

Figure 35:
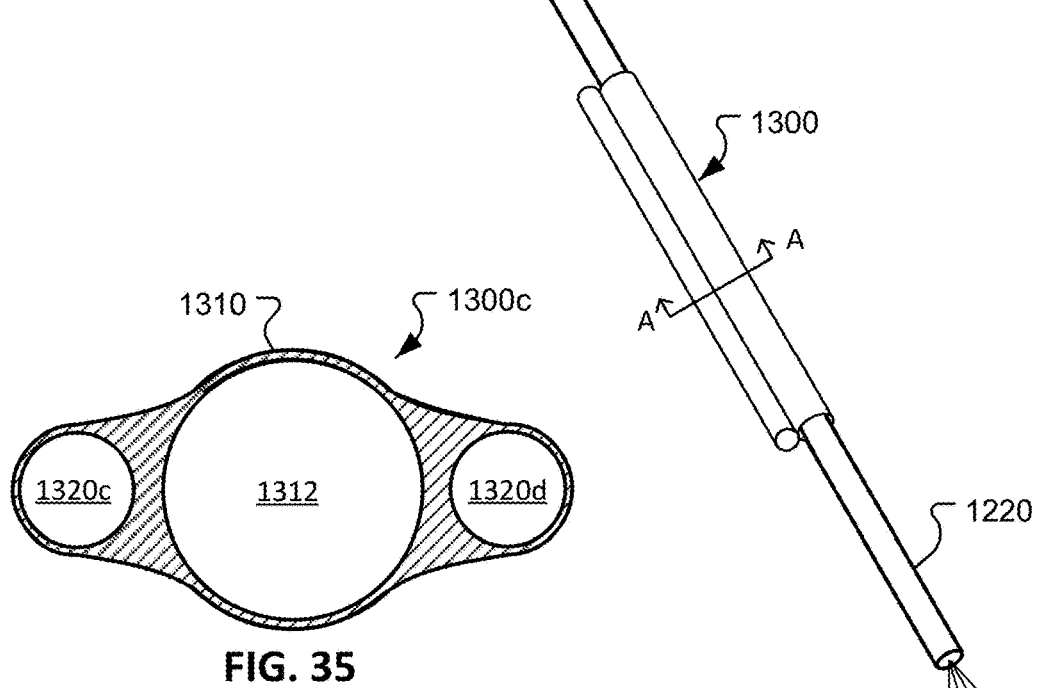
FIG. 35 shows another example transverse cross-sectional view of the removable sleeve device of FIG. 32.
Figure 33:
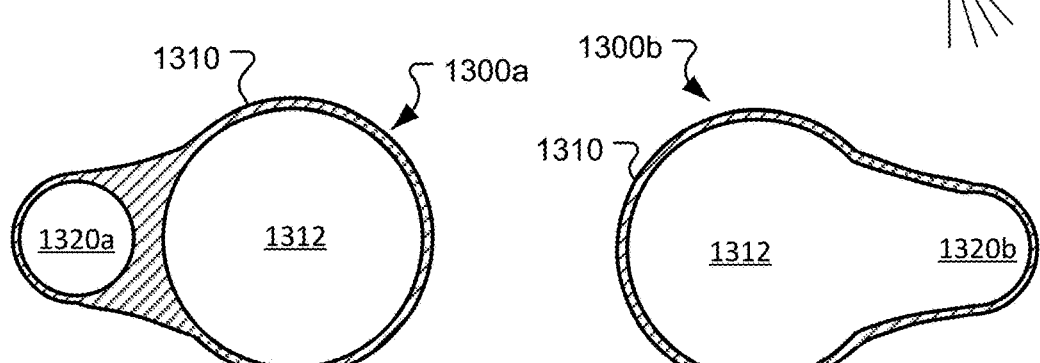
FIG. 33 shows an example transverse cross-sectional view of the removable sleeve device of FIG. 32.
Figure 34:
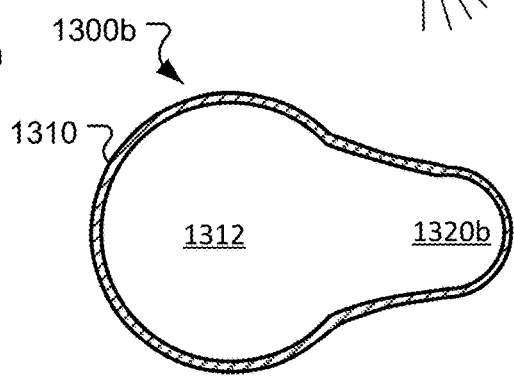
FIG. 34 shows another example transverse cross-sectional view of the removable sleeve device of FIG. 32.

FIGS. 33-35 are non-limiting example transverse cross-sectional views of the sleeve device 1300, taken at section A-A. FIG. 33 depicts a transverse cross-sectional view of a sleeve device 1300a. FIG. 34 depicts a transverse cross-sectional view of a sleeve device 1300b. FIG. 35 depicts a transverse cross-sectional view of a sleeve device 1300c.

Each of the sleeve devices 1300a-c includes a primary tube 1310 that defines a lumen 1312. The lumen 1312 is configured to slidably receive the shaft 1220 of the instrument 1200 (as shown in FIG. 32). While the sleeve devices 1300a-c are slidingly coupled to the shaft 1220, the sleeve devices 1300a-c can be adjustably affixed at various locations along the length of the shaft 1220. In some embodiments, a mechanism that provides a light compression between sleeve devices 1300a-c and the shaft 1220 can be included to adjustably affix the sleeve devices 1300a-c at various locations along the length of the shaft 1220. For example, such a mechanism can comprise a collet, an annular elastomeric interface member, a wedge, a clasp, a clamp, and the like, without limitation.

The sleeve devices 1300a-c each define one or more auxiliary working channels that can receive and guide an additional instrument(s). For example, sleeve device 1300a (FIG. 33) defines a single auxiliary working channel 1320a. The sleeve device 1300b (FIG. 34) also defines a single auxiliary working channel 1320b. The sleeve device 1300c (FIG. 35) defines a first auxiliary working channel 1320c and a second auxiliary working channel 1320d.

The auxiliary working channel 1320a of the sleeve device 1300a is separated from the lumen 1312 by a material portion of the sleeve device 1300a as shown in FIG. 33. In contrast, the auxiliary working channel 1320b of the sleeve device 1300b is confluent (open, continuous) with the lumen 1312 as shown in FIG. 34. The auxiliary working channels 1320c and 1320d of the sleeve device 1300c are separated from the lumen 1312 as shown in FIG. 35. It should be understood that any arrangement and combinations of arrangements are envisioned and within the scope of this disclosure. The sizes and cross-sectional shapes of the auxiliary working channels 1320a-b can be made in any desired manner, without limitation.

Figure 36:
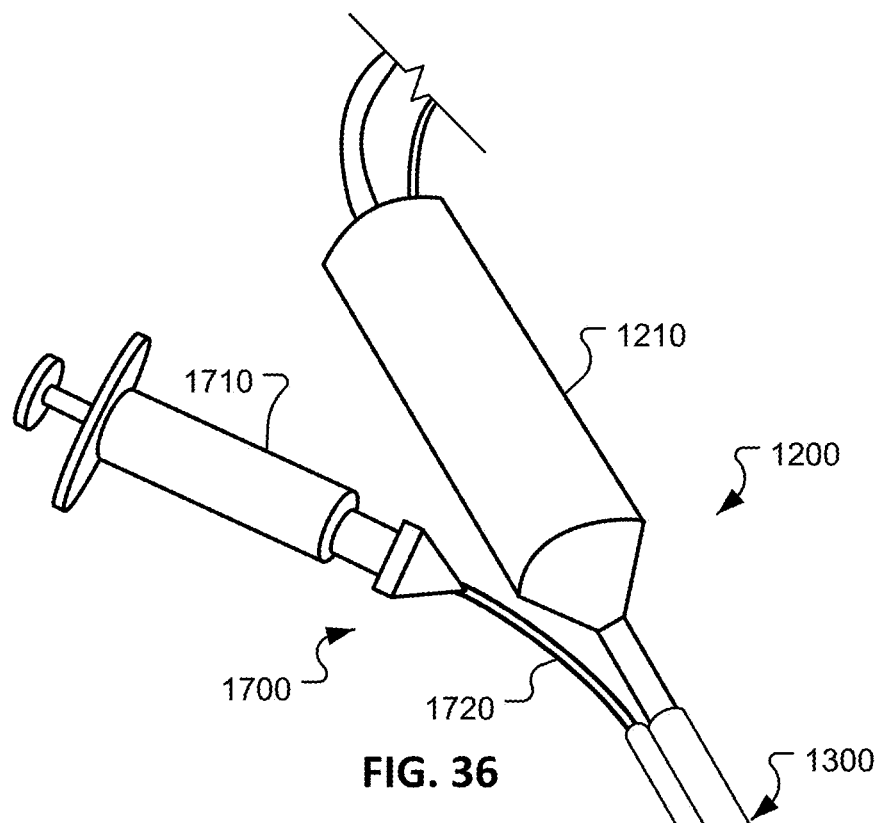
FIG. 36 shows an example injector system, implant refill system, or sample extraction system used with the removable sleeve device of FIG. 32.

FIG. 36 shows an example system that includes the otologic instrument 1200 (e.g., an endoscope in the depicted embodiment), the sleeve device 1300 (coupled to the shaft 1220 of the endoscope 1200), and an example injector device, implant delivery device, implant refill device, or sample extraction device 1700 that is also extending through the sleeve device 1300. The injector device, implant delivery device, implant refill device, or sample extraction device 1700 (referred to hereafter as the device 1700), represents multiple types of devices. For example, in some embodiments the device 1700 is an injector device that can deliver a formulation to a target location in the middle and/or inner ear regions. In some embodiments, the device 1700 is an implant delivery device that can deliver an implant to a target location in the middle and/or inner ear regions. Thereafter, the implant can deliver a formulation at the target location in the middle and/or inner ear regions. In some embodiments, the device 1700 is an implant refill device. Such an implant refill device can deliver a replenishment of a formulation to a previously-implanted device, while the device is located in vivo at a target location in the middle and/or inner ear regions. In some embodiments, the device 1700 is a sample extraction device for drawing a tissue and/or fluid sample from a target location in the middle and/or inner ear regions.

The device 1700 includes an actuator 1710 and a shaft 1720 extending from the actuator 1710. In the depicted embodiment, the actuator 1710 is depicted as a syringe, but other types of actuators 1710 can be substituted depending on the functionality of the device 1700. The shaft 1720 is depicted as a tube, needle or cannula, but other types of shafts 1720 can be substituted depending on the functionality of the device 1700.

In the depicted embodiment, the shaft 1720 includes a naturally-curved distal tip portion (or deflectable distal tip portion). Such a curved distal tip portion can be used for delivering formulations etc. off-axis relative to the main viewing axis of the endoscope 1200. Once the distal tip portion of the shaft 1720 is advanced past the distal tip of the endoscope shaft 1220, the shaft 1720 can be rotated freely with respect to the endoscope shaft 1220. Although shown with a curved tip to the cannula, in other embodiments the shaft is straight.

Figure 37:
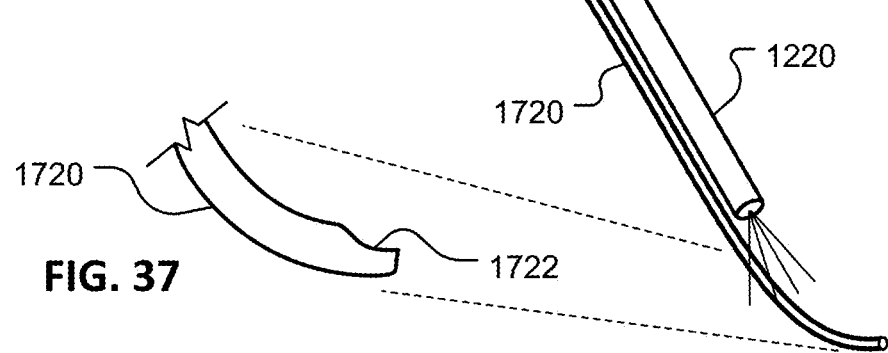
FIG. 37 shows an example distal tip portion of the example injector system, implant refill system, or sample extraction system of FIG. 36.

In one embodiment, as depicted in FIG. 37, the distal tip of the shaft 1720 can have a curved notch 1722 to assist in maintaining the orientation of the tip of the shaft 1720 such that it doesn't rotate "outwards" before passing the tip of the endoscope shaft 1220 (which might otherwise induce trauma to the tympanic membrane or other adjacent tissues if the tip of the shaft 1720 extended laterally away from the endoscope shaft 1220 as advanced).

Figure 38:
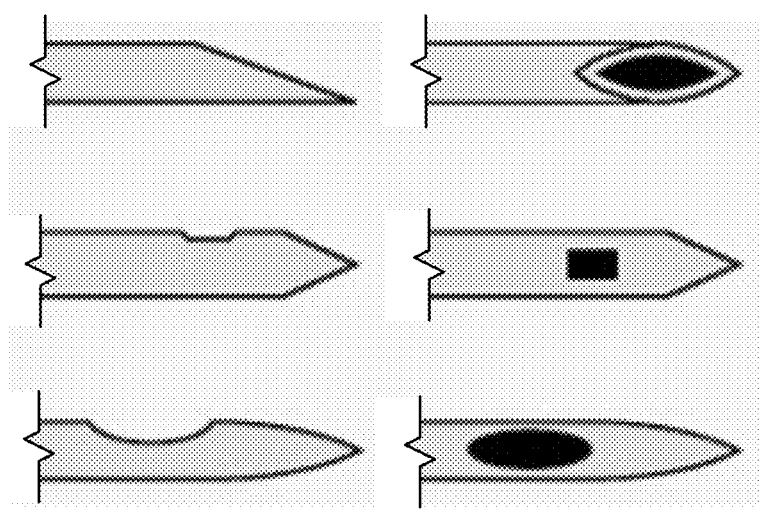
FIG. 38 shows various example distal tip portions of a needle or cannula of the example injector system, implant refill system, or sample extraction system of FIG. 36.
Figure 39:
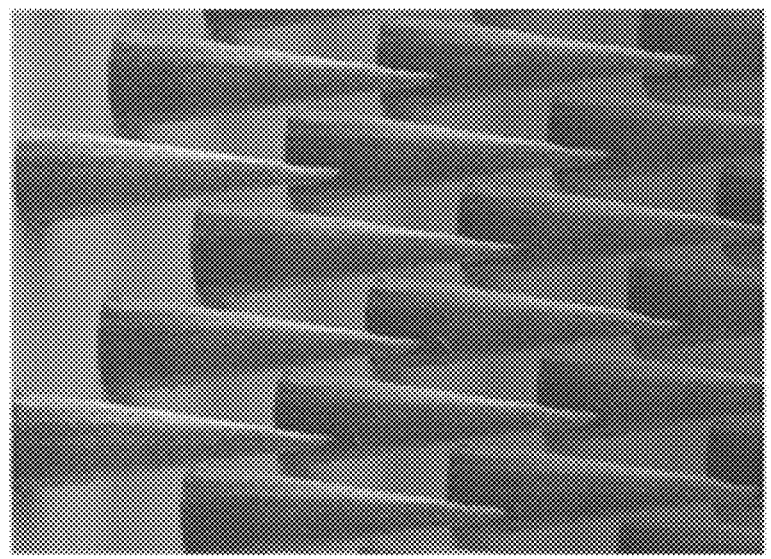
FIG. 39 shows an example microneedle array of a needle or cannula of the example injector system, implant refill system, or sample extraction system of FIG. 36.

In some embodiments, the distal end portion of the shaft 1720 can be a small-gauge needle or cannula tip that is beveled, flat, rounded, side-cut, notched, atraumatic, etc., as shown in various non-exhaustive examples in FIG. 38, or can have the form of a microneedle array as shown in FIG. 39. In other embodiments, the distal end portion of the shaft 1720 can have a blunt, atraumatic, soft polymer tip. While the distal end portion of the shaft 1720 is configured for delivering formulations to the middle and/or inner ear, in some embodiments the distal end portion of the shaft 1720 terminates at a distal tip that can be used to extract, replace, or refill an implant device.

In another embodiment, the distal end portion of the shaft 1720 terminates at a distal tip that defines a port through which suction is applied. The port at the distal tip is activated by a device to generate the suction (such as manually pulling back on the syringe 1710, or through mechanically, electronically, pneumatically, or hydraulically-aided action), which can for example extract 1-100 microliter volume of perilymph for diagnostic purposes. In another example embodiment, the device 1700 can be used to extract samples from a soft tissue lesion for analysis.

Figure 40:
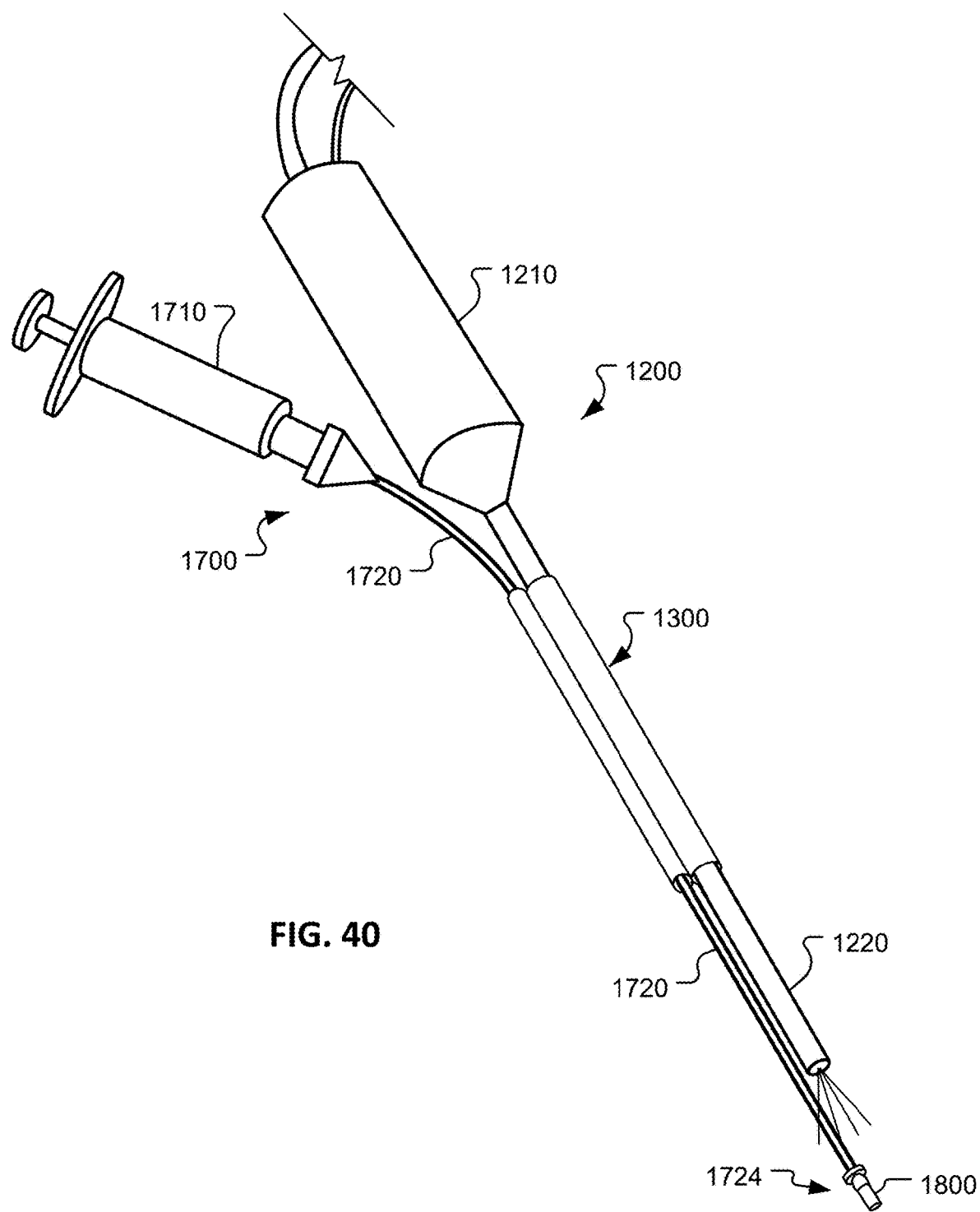
FIG. 40 shows an example implant delivery system used with the removable sleeve device of FIG. 32.

Referring now to FIG. 40, in the depicted embodiment the distal end portion of the instrument 1700 terminates at a distal tip 1724 that defines a port to which an example implant 1800 is releasably coupled. In some embodiments, the implant 1800 can be slip-fit into the tip 1724 of a through-channel at the distal tip 1724 of the delivery instrument 1700. In other embodiments, the implant 1800 can be held by the cannula shaft 1720 via suction force.

The instrument 1700 can be controlled by a clinician to position the distal tip 1724 and the releasably coupled implant 1800 at a target location in the middle and/or inner region. For example, in some embodiments the distal tip 1724 and the releasably coupled implant 1800 can be positioned at the round window niche, the oval window, or to other parts of the cochlea through a cochleostomy.

In some embodiments, the implant 1800 can be deployed from the delivery instrument 1700 via exterior features on the implant 1800 which engage the target tissue and exceed the slip-fit force within the instrument 1700. In some embodiments, the implant 1800 can be deployed from the delivery instrument 1700 by active pushing of the implant 1800 from the cannula shaft 1720 by air pressure or by an extendable central core wire, or by cutting off the suction to the cannula shaft 1720. In some implementations, the implant 1800 is deployed completely in the middle ear, between the middle ear and the inner ear, or completely in the inner ear.

In some embodiments, the implant 1800 can be solid or semisolid (example biocompatible implant materials include silicone, polyglycolide, polylactide, polycaprolactone, PEG, polyurethane, and ethylene vinyl acetate) with therapeutic agents dispersed within. In some embodiments, the implant 1800 can be comprised of a solid drug matrix surrounded by drug permeable materials (for example ethylene vinyl acetate, polyurethane) and/or drug impermeable materials (for example polysulfone, polyvinyl alcohol, PMMA, polyimide, and metals such as titanium, stainless steel, and nitinol) for controlling drug release.

In some embodiments, the implant 1800 can be comprised of a metal or polymer core with a drug eluting coating applied. Example coating materials include, but are not limited to, biodegradable polymers such as polyphosphorylcholine, PLA, PGA, PLGA, polycaprolactone, and durable polymers such as PBMA and EVA. In some embodiments, the implant 1800 can be permanent or dissolve over time. In some embodiments, the implant 1800 can contain a reservoir to house a solid, gel or liquid formulation of one or more therapeutic agents having one or more active ingredients.

In some embodiments, the implant 1800 can contain electrodes or be a cochlear implant. In some embodiments, the implant 1800 can comprise an array of microneedles that act as a permeation enhancer. In some embodiments, the implant 1800 can consist of a patch that seals perilymph leakage on the oval window or the round window to prevent or treat a perilymph fistula.

The formulation delivered by the devices, systems, and methods as described herein can be a gel, a spray, a mist, a liquid, a paste, a solution, a suspension, an emulsification, and so on, without limitation. In some embodiments, the formulation can contain permeation enhancers or magnetic microparticles to improve the rate of diffusion of the therapeutic agent(s) into the inner ear. In certain embodiments, the formulation can contain lipid encapsulated agents, microparticles, or viral vectors, to improve the efficiency and/or extend the duration of the delivery of the therapeutic agent(s) into the inner ear. In particular embodiments, the formulation can contain contrast agents, dyes or stains for diagnostic imaging of the middle and inner ear. In some embodiments, the formulation can comprise or consist of a gel or another material that seals perilymph leakage on the oval window or the round window to treat or prevent a perilymph fistula.

In some embodiments, the formulation or otic composition (e.g., an extended release otic composition) can be delivered to a subject from or with the help of the treatment devices described herein. Such a formulation may be delivered using an implantable formulation carrier such as an implant device, or by directly injecting or otherwise delivering the formulation.

In some embodiments, an extended release formulation can include a polymer composition that can form a gel. For example, a polymer composition can include a functional polymer, wherein the functional polymer includes a first functional group, and a crosslinker, wherein the crosslinker includes a second functional group, and water, wherein a crosslinking reaction can occur between the first functional group and the second functional group to form a gel. In some embodiments, the functional polymer can be present in an amount of about 5% to about 15% by weight of the polymer composition. In some embodiments, the crosslinker can be present in an amount of about 0.2% to about 0.6% by weight of the polymer composition.

It will be appreciated that a first functional group (e.g., on a functional polymer) and a second functional group (e.g., on a crosslinker) should be such that a crosslinking reaction can occur. Therefore, the choice of functional polymer can be based on the choice of crosslinker, or vice versa. In some embodiments, a first functional group can be an N-hydroxysuccinimide (NHS) group and a second functional group can be an amine (e.g., a primary amine), or vice versa. In some cases, the functional polymer contains only electrophilic or nucleophilic functional groups, and the crosslinker contains only nucleophilic or electrophilic functional groups, respectively.

In some embodiments, the functional polymer is a multi-arm (e.g., 3-arm, 4-arm, 6-arm, or 8-arm) polyethylene glycol (PEG) including two more succinimidyl ester (e.g., a succinimidyl succinate or a succinimidyl glutarate) or sulfo-succinimidyl ester functional groups and the crosslinker contains a plurality of amine (e.g., primary amine) functional groups. In some embodiments, the multi-arm PEG can have two or more arms terminate in a succinimidyl ester functional group. In some embodiments, one or monomers of the multi-arm PEG can include a succinimidyl ester functional group. In some embodiments, the crosslinker can be a polylysine (e.g., an epsilon-polylysine) (e.g., trilysine, tetralysine, or pentalysine). For example, in some embodiments, the functional polymer can be pentaerythritol poly (ethylene glycol) ether tetrasuccinimidyl glutarate, and the crosslinker can be trilysine.

In some embodiments, the functional polymer is a multi-arm (e.g., 3-arm 4-arm, 6-arm, or 8-arm) polyethylene glycol including two or more amine (e.g., primary amine) functional groups and the crosslinker includes a plurality of succinimidyl ester (e.g., a succinimidyl succinate or succinimidyl glutarate) or sulfo-succinimidyl ester functional groups. In some embodiments, the multi-arm PEG can have two or more arms terminate in an amine (e.g., primary amine) functional group. In some embodiments, one or more monomers of the multi-arm PEG can include an amine (e.g., primary amine) functional group. In some embodiments, the crosslinker can be disuccinimidyl glutarate, disuccinimidyl suberate, bis(sulfosuccinimidyl)suberate, or disuccinimidyl succinate.

In some embodiments, an extended release otic composition can include an active agent (e.g., a therapeutic agent, a prophylactic agent, a diagnostic or visualization agent, or a combination thereof). An active agent can include, for example, a protein (e.g., an enzyme, a growth factor, an antibody or an antigen-binding fragment thereof), a carbohydrate (e.g., a glycosaminoglycan), a nucleic acid (e.g., an antisense oligonucleotide, an aptamer, a micro RNA, a short interfering RNA, or a ribozyme), small molecules, or combinations thereof. In some embodiments, a small molecule can include an antibiotic, an antineoplastic agent (e.g., doxorubicin), a local anesthetic, a steroid, a hormone, an apoptotic inhibitor (for example, an inhibitor of Apaf-1; see, e.g., U.S. Pat. No. 9,040,701, incorporated by reference herein in its entirety), an angiogenic agent, an anti-angiogenic agent (e.g., a VEGF inhibitor), a neurotransmitter, a psychoactive drug, an anti-inflammatory, and combinations thereof.

In some embodiments, an active agent of the formulation can include an anti-angiogenic agent. In some embodiments, an anti-angiogenic agent can be a VEGF inhibitor. In some cases, a VEGF inhibitor can be an antibody or an antigen-binding fragment thereof, a decoy receptor, a VEGFR kinase inhibitor, an allosteric modulator of a VEGFR, or a combination thereof. In some cases, a VEGF inhibitor can be an antibody or an antigen-binding fragment thereof. For example, in some embodiments, a VEGF inhibitor can be alacizumab, bevacizumab (AVASTIN®), icrucumab (IMC-18F1), ramucirumab (LY3009806, IMC-1121B, CYRAMZA®), or ranibizumab (LUCENTIS®). In some embodiments, a VEGF inhibitor can be a decoy receptor (e.g., aflibercept). In some embodiments, a VEGF inhibitor can be a VEGFR kinase inhibitor, such as agerafenib, altiratinib, apatinib, axitinib, cabozantinib, cediranib, lapatinib, lenvatinib, motesanib, nintedanib, pazopanib, pegaptanib, rebastinib, regorafenib, semaxanib, sorafenib, sunitinib, toceranib, tivozanib, or vandetanib. Other examples of VEGF inhibitors may be known in the art. In some embodiments, a VEGFR inhibitor can be an allosteric modulator of a VEGFR (e.g, cyclotraxin B).

An extended release formulation or otic composition can, in some cases, be useful to treat an otic disease or disorder, such as Meniere's Disease (MD), Autoimmune Inner Ear Disease (AIED), sudden sensorineural hearing loss (SSNHL), noise-induced hearing loss (NIHL), age-related hearing loss, sensorineural hearing loss associated with diabetes, tinnitus, damaged cilia from an autoimmune disorder, damaged cilia from an infection, damaged cilia from excess fluid or pressure, hearing loss due to chemotherapy, or a combination thereof.

Formulations that can be delivered from or with the help of the treatment devices described herein can also include but are not limited to antioxidants, anti-inflammatories, steroids, antimicrobials, NMDA receptor antagonists, nootropics, anti-apoptotic agents, neurotrophins, neuroprotective agents, neural protective proteins such as CNTF, BDNF, PEDF, NGF, and the like, cannabinoids, monoclonal antibodies, other proteins, gene therapy, iRNA, tyrosine kinase inhibitors (TKIs), dual leucine zipper kinase (DLK) inhibitors, and protein therapies like anti-VEGF.

As an example, the therapeutic agent of the formulation can include, but is not limited to antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; antibacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; keratolytic agents such as selenium sulfide, imiquimod, salicylic acid, and retinoids; antioxidants, NMDA receptor antagonists, nootropics, anti-apoptotic agents, neurotrophins, neuroprotective agents, tyrosine kinase inhibitors (TKIs), dual leucine zipper kinase (DLK) inhibitors, cannabinoids, monoclonal antibodies, antibody fragments, other proteins, and gene therapy. Other therapeutic agents known to those skilled in the art which are capable of controlled, sustained release into the ear in the manner described herein are also suitable for use in accordance with embodiments of the devices described herein.

The therapeutic agent of the formulation can include, but is not limited to sodium thiosulfate to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone and other corticosteroids for the treatment of Meniere's Disease and forms of hearing loss associated with inflammation; D-methionine (Southern Illinois University) to protect against Noise-induced hearing loss; LY411575 (a selective gamma secretase inhibitor that blocks Notch activation); and NT-3 neurotrophic factor.

The therapeutic agent of the formulation can include, but is not limited to local anesthetics for delivery into the ear canal including benzocaine, antipyrine, butamben, dibucaine, lidocaine, prilocaine, oxybuprocaine, pramoxine, proparacaine, proxymetacaine, and tetracaine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, hyaluronic acid, sodium hyaluronate, sodium alginate, poly(vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, emulsifying agents or other related materials.

A therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

While the devices, systems, materials, compounds, compositions, articles, and methods described herein described in the context of treating hearing loss, it should be understood that the devices, systems, materials, compounds, compositions, articles, and methods may be used to treat any disorder of the middle ear and/or inner ear including, but not limited to, tinnitus, balance disorders including vertigo, Meniere's Disease, vestibular neuronitis, vestibular schwannoma, labyrinthitis, otosclerosis, ossicular chain dislocation, cholesteatoma, otitis media, middle ear infections, and tympanic membrane perforations, to provide a few examples.

Although the round window membrane is one target site for therapeutic agent delivery or access, the systems and methods described herein can also be used for precise delivery of therapeutic agents to other target sites, such as the oval window or other parts of the middle ear cavity, and for providing access to other features or regions of the middle ear. For example, the systems and methods described herein can be used for minimally invasive surgical reconstruction of the ossicular chain, for removal of cholesteatoma, for diagnostic assessment, and other procedures. Any and all such techniques for using the systems and methods described herein are included within the scope of this disclosure.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

A number of embodiments have been described. Nevertheless, it will be understood that various modifications may be made without departing from the claim scope here. Accordingly, other embodiments are within the scope of the following claims.

What is claimed is:

1. A system for delivering a therapeutic gel formulation to a round window niche of a cochlea under direct endoscopic visualization, the system comprising:
   an endoscope including an endoscope shaft with a distal tip portion sized to be positioned within a middle ear;
   a sleeve device defining: (i) a first lumen through which the endoscope shaft extends such that the distal tip portion of the endoscope is positionable through a tympanic membrane and into a middle ear to visualize a round window niche of a cochlea while the sleeve device is entirely external from the tympanic membrane, and (ii) a second lumen adjacent to the first lumen;
   a gel injection device including a proximal actuator and an injection shaft with an injector distal tip portion defining a side-cut delivery port positioned proximally of a distal-most end of the injection shaft to dispense a therapeutic gel formulation, the injection shaft sized to be slidably received in the second lumen of the sleeve device while the endoscope shaft is slidably received in the first lumen of the sleeve device, wherein the injector distal tip portion of the gel injection device is positionable through the tympanic membrane and movable distally of the distal tip portion of the endoscope such that the side-cut delivery port of the gel injection device is advanceable to the round window niche to dispense the therapeutic gel formulation to the round window niche while the distal tip portion of the endoscope is spaced proximally from the side-cut delivery port of the injection injector shaft to provide visualization of the injection; and
   a gel formulation source in fluid communication with the gel injection device so that the side-cut delivery port is configured to deliver the therapeutic gel formulation at the round window niche in response to movement of the proximal actuator of the gel injection device.

2. The system of claim 1, wherein the injector distal tip portion of the gel injection device is adjustable from a longitudinally straight shape to a curved shape to orient the side-cut delivery port toward the round window niche.

3. The system of claim 2, wherein the injector distal tip portion of the gel injection device is selectively adjustable to the curved shape by manipulating one or more control members slidably coupled with the injector distal tip portion.

4. The system of claim 1, further comprising a first tympanic membrane port device configured to be removably implanted in the tympanic membrane, wherein the first membrane port device defines a port lumen, and wherein at least one of the endoscope and the gel injection device is configured to pass through the port lumen.

5. The system of claim 1, wherein the sleeve device is a two-channel alignment sleeve in which the first lumen is a primary channel having a first diameter and the second lumen is an auxiliary working channel having a second diameter smaller than the first diameter and being laterally separated from the primary channel by an intermediate wall portion of the two-channel alignment sleeve.

6. The system of claim 5, wherein the injector distal tip portion of the gel injection device is movable relative to both the two-channel alignment sleeve and the distal tip portion of the endoscope.

7. The system of claim 6, wherein a proximal portion of the gel injection device located proximally of the two-channel alignment sleeve has a curved shape.

8. The system of claim 7, wherein the injection shaft of the gel injection device comprises a needle.

9. The system of claim 7, wherein the endoscope shaft has an outer diameter larger than an outer diameter of the injection shaft and is sized to pass through a first incision through the tympanic membrane.

10. The system of claim 9, wherein the outer diameter of the injection shaft is sized to pass through a second incision through the tympanic membrane while positioned adjacent to the endoscope shaft.

11. The system of claim 10, further comprising at least one tympanic membrane port device configured to be removably implanted in the tympanic membrane, the tympanic membrane port device including a central port lumen having a diameter of 1 mm.

12. The system of claim 10, wherein the endoscope shaft is positionable through the tympanic membrane via an opening having a diameter of 1 mm.

13. The system of claim 5, wherein the two-channel alignment sleeve is configured to compress against an exterior of the endoscope to affix the two-channel alignment sleeve to the endoscope while the endoscope shaft is positioned with the primary channel so that the injector distal tip portion of the injection shaft is movable relative to both the two-channel alignment sleeve and the distal end portion of the endoscope.

14. The system of claim 1, wherein the gel formulation source comprises a syringe reservoir containing the therapeutic gel formulation comprising an anti-inflammatory agent.

15. The system of claim 14, wherein the therapeutic gel formulation comprising the anti-inflammatory agent comprises first and second functional components mixed to generate a crosslinking reaction of the therapeutic gel formulation.

16. The system of claim 14, wherein the therapeutic gel formulation contained within the syringe reservoir comprises the anti-inflammatory agent selected from group consisting of: hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone.

17. The system of claim 14, wherein the anti-inflammatory agent of the therapeutic gel formulation is provided in an amount sufficient to move passively by diffusion across a membrane of the round window and into the cochlea.

* * * * *